United States Patent
Ward et al.

(10) Patent No.: US 11,911,551 B2
(45) Date of Patent: Feb. 27, 2024

(54) METHOD FOR TREATING DRUG INTOXICATION

(71) Applicant: ExThera Medical Corporation, Martinez, CA (US)

(72) Inventors: Robert S. Ward, Orinda, CA (US); Keith R. McCrea, Concord, CA (US)

(73) Assignee: ExThera Medical Corporation, Martinez, CA (US)

( * ) Notice: Subject to any disclaimer, the term of this patent is extended or adjusted under 35 U.S.C. 154(b) by 843 days.

(21) Appl. No.: 17/006,163

(22) Filed: Aug. 28, 2020

(65) Prior Publication Data

US 2021/0008269 A1 Jan. 14, 2021

Related U.S. Application Data

(63) Continuation-in-part of application No. 15/446,822, filed on Mar. 1, 2017, now Pat. No. 10,786,615.

(Continued)

(51) Int. Cl.
*A61M 1/36* (2006.01)
*B01J 20/20* (2006.01)
(Continued)

(52) U.S. Cl.
CPC ........ *A61M 1/3679* (2013.01); *B01D 15/3828* (2013.01); *B01J 20/20* (2013.01);
(Continued)

(58) Field of Classification Search
CPC ........ A61M 1/3679; A61M 2202/0014; A61M 2202/0413; A61M 2202/049; B01J 20/20;
(Continued)

(56) References Cited

U.S. PATENT DOCUMENTS

| 3,782,382 A | 1/1974 | Naftulin et al. |
| 4,048,064 A | 9/1977 | Clark, III |

(Continued)

FOREIGN PATENT DOCUMENTS

| CN | 1395620 A | 2/2003 |
| CN | 101370536 A | 2/2009 |

(Continued)

OTHER PUBLICATIONS

Abdul-Razzak, K. et al., "Fetal and newborn calf thymus as a source of chromatin proteins: Purification of HMG-1 and HMG-2," Preparative Biochemistry and Biotechnology, 17(1):51-61, 1987.

(Continued)

*Primary Examiner* — John Kim
(74) *Attorney, Agent, or Firm* — Kilpatrick Townsend & Stockton LLP

(57) ABSTRACT

Methods and devices are disclosed for the treatment of a subject suffering from drug intoxication by cleansing a contaminated sample from the subject with adsorption media. The adsorption media composition is selected for its antithrombogenic properties and for its ability to adhere to one or more drug targets to be reduced or eliminated. The media can further be held in a cartridge for use in extracorporeal treatments such as those of hemoperfusion. Contacting the contaminated sample from the subject with the absorption medium allows for the separation of a portion of the drug target from the sample, producing a cleansed sample that can be infused into the subject.

16 Claims, 8 Drawing Sheets

Related U.S. Application Data

(60) Provisional application No. 62/302,329, filed on Mar. 2, 2016.

(51) Int. Cl.
  *B01J 20/26* (2006.01)
  *B01J 20/28* (2006.01)
  *B01J 20/32* (2006.01)
  *B01D 15/38* (2006.01)
  *B01J 20/24* (2006.01)

(52) U.S. Cl.
  CPC ............ *B01J 20/24* (2013.01); *B01J 20/264* (2013.01); *B01J 20/28019* (2013.01); *B01J 20/28023* (2013.01); *B01J 20/3274* (2013.01); *A61M 2202/0014* (2013.01); *A61M 2202/049* (2013.01); *A61M 2202/0413* (2013.01); *B01J 2220/46* (2013.01); *B01J 2220/4806* (2013.01); *B01J 2220/4825* (2013.01)

(58) Field of Classification Search
  CPC . B01J 20/24; B01J 20/048; B01J 20/08; B01J 20/103; B01J 20/12; B01J 20/18; B01J 20/28019; B01J 20/28023; B01J 20/321; B01J 20/3212; B01J 20/3274; B01J 20/205; B01J 20/264; B01J 20/261; B01J 20/3204; B01J 2220/46; B01J 2220/4806; B01J 2220/4825; B01D 15/3828; A61K 35/14
  See application file for complete search history.

(56) References Cited

U.S. PATENT DOCUMENTS

| | | | |
|---|---|---|---|
| 4,103,685 A | 8/1978 | Lupien et al. |
| 4,358,376 A | 11/1982 | Moriuchi et al. |
| 4,415,665 A | 11/1983 | Mosbach et al. |
| 4,430,496 A | 2/1984 | Abbott |
| 4,599,165 A | 7/1986 | Chevallet |
| 4,613,665 A | 9/1986 | Larm |
| 4,637,994 A | 1/1987 | Tani et al. |
| 4,643,896 A | 2/1987 | Asakura et al. |
| 4,820,302 A | 4/1989 | Woodroof |
| 4,955,870 A | 9/1990 | Ridderheim et al. |
| 5,116,962 A | 5/1992 | Stueber et al. |
| 5,211,850 A | 5/1993 | Shettigar et al. |
| 5,227,049 A | 7/1993 | Chevallet et al. |
| 5,318,511 A | 6/1994 | Riquier et al. |
| 5,403,917 A | 4/1995 | Boos et al. |
| 5,437,861 A | 8/1995 | Okarma et al. |
| 5,447,859 A | 9/1995 | Prussak |
| 5,476,509 A | 12/1995 | Keogh, Jr. et al. |
| 5,679,775 A | 10/1997 | Boos et al. |
| 5,753,227 A | 5/1998 | Strahilevitz |
| 5,773,384 A | 6/1998 | Davankov et al. |
| 5,858,238 A | 1/1999 | McRea |
| 6,037,458 A | 3/2000 | Hirai et al. |
| 6,159,377 A | 12/2000 | Davankov et al. |
| 6,197,568 B1 | 3/2001 | Marks et al. |
| 6,238,795 B1 | 5/2001 | Strom |
| 6,248,127 B1 | 6/2001 | Shah et al. |
| 6,312,907 B1 | 11/2001 | Guo et al. |
| 6,461,665 B1 | 10/2002 | Scholander |
| 6,544,727 B1 | 4/2003 | Hei |
| 6,559,290 B1 | 5/2003 | Nakatani et al. |
| 6,653,457 B1 | 11/2003 | Larm et al. |
| 7,179,660 B1 | 2/2007 | Kirakossian |
| 7,408,045 B2 | 8/2008 | Maruyama et al. |
| 7,695,609 B2 | 4/2010 | Soundarrajan et al. |
| 8,273,357 B2 | 9/2012 | Hacohen et al. |
| 8,663,148 B2 | 3/2014 | Larm et al. |
| 8,758,286 B2 | 6/2014 | Ward et al. |
| 9,173,989 B2 | 11/2015 | Larm et al. |
| 9,408,962 B2 | 8/2016 | Ward et al. |
| 9,669,150 B2 | 6/2017 | Larm et al. |
| 9,764,077 B2 | 9/2017 | Larm et al. |
| 10,086,126 B2 | 10/2018 | Ward et al. |
| 10,188,783 B2 | 1/2019 | Larm et al. |
| 10,457,974 B2 | 10/2019 | Ward et al. |
| 10,487,350 B2 | 11/2019 | Ward et al. |
| 10,537,280 B2 | 1/2020 | McCrea et al. |
| 10,639,413 B2 | 5/2020 | McCrea et al. |
| 10,688,239 B2 | 6/2020 | Larm et al. |
| 10,786,615 B2 | 9/2020 | Ward et al. |
| 10,857,283 B2 | 12/2020 | Ward et al. |
| 11,065,378 B2 | 7/2021 | Larm et al. |
| 11,123,466 B2 | 9/2021 | Ward et al. |
| 11,266,772 B2 | 3/2022 | McCrea et al. |
| 11,306,346 B2 | 4/2022 | Ward et al. |
| 2001/0005487 A1 | 6/2001 | Kamibayashi et al. |
| 2002/0018985 A1 | 2/2002 | Eible et al. |
| 2002/0040012 A1 | 4/2002 | Stiekema et al. |
| 2002/0058032 A1 | 5/2002 | Hirai et al. |
| 2002/0068183 A1 | 6/2002 | Huang et al. |
| 2002/0197249 A1 | 12/2002 | Brady et al. |
| 2002/0197252 A1 | 12/2002 | Brady et al. |
| 2003/0021780 A1 | 1/2003 | Smith et al. |
| 2003/0044769 A1 | 3/2003 | Ogino et al. |
| 2003/0148017 A1 | 8/2003 | Tuominen et al. |
| 2003/0231981 A1 | 12/2003 | Johnson et al. |
| 2004/0054320 A1 | 3/2004 | Kissinger et al. |
| 2004/0084358 A1 | 5/2004 | O'Mahony et al. |
| 2004/0115278 A1 | 6/2004 | Putz et al. |
| 2004/0140265 A1 | 7/2004 | Lihme |
| 2004/0176672 A1 | 9/2004 | Silver et al. |
| 2004/0182783 A1 | 9/2004 | Walker et al. |
| 2004/0185553 A9 | 9/2004 | Hei |
| 2004/0202783 A1 | 10/2004 | Baumann et al. |
| 2005/0098500 A1 | 5/2005 | Collins et al. |
| 2005/0142542 A1 | 6/2005 | Hei et al. |
| 2005/0205476 A1 | 9/2005 | Chevallet et al. |
| 2005/0244371 A1 | 11/2005 | Lentz |
| 2005/0271653 A1 | 12/2005 | Strahilevitz |
| 2005/0281809 A1* | 12/2005 | Roberts ............... A61M 1/3486 424/140.1 |
| 2006/0030027 A1 | 2/2006 | Ellson et al. |
| 2006/0076295 A1 | 4/2006 | Leonard |
| 2006/0093999 A1 | 5/2006 | Hei |
| 2006/0134595 A1 | 6/2006 | Rapp |
| 2006/0252054 A1 | 11/2006 | Ping |
| 2007/0190050 A1 | 8/2007 | Davidner et al. |
| 2007/0218514 A1 | 9/2007 | Smith et al. |
| 2007/0231217 A1 | 10/2007 | Clintone et al. |
| 2008/0021365 A1 | 1/2008 | Kobayashi et al. |
| 2008/0138434 A1 | 6/2008 | Brady et al. |
| 2008/0268464 A1 | 10/2008 | Schumacher et al. |
| 2008/0314817 A1 | 12/2008 | Fujita et al. |
| 2009/0105194 A1 | 4/2009 | Flengsrud et al. |
| 2009/0136586 A1 | 5/2009 | Larm et al. |
| 2009/0173685 A1 | 7/2009 | Imai et al. |
| 2009/0186065 A1 | 7/2009 | Tillman et al. |
| 2009/0206038 A1 | 8/2009 | Thomas |
| 2009/0246800 A1 | 10/2009 | Mattingly et al. |
| 2009/0325276 A1 | 12/2009 | Battrell |
| 2010/0021622 A1 | 1/2010 | Meng et al. |
| 2010/0040546 A1 | 2/2010 | Hyde et al. |
| 2010/0069816 A1 | 3/2010 | Brady et al. |
| 2010/0079360 A1 | 4/2010 | McLaughlin et al. |
| 2010/0098666 A1 | 4/2010 | Wright |
| 2010/0112725 A1 | 5/2010 | Babu et al. |
| 2010/0145317 A1 | 6/2010 | Laster et al. |
| 2010/0216226 A1 | 8/2010 | Hyde et al. |
| 2010/0217173 A1 | 8/2010 | Hyde et al. |
| 2010/0239673 A1 | 9/2010 | Linhardt |
| 2010/0249689 A1 | 9/2010 | Larm et al. |
| 2010/0276359 A1 | 11/2010 | Ippommatsu et al. |
| 2010/0291588 A1 | 11/2010 | McDevitt |
| 2010/0326916 A1 | 12/2010 | Wrazel et al. |
| 2011/0137224 A1 | 6/2011 | Ibragimov |
| 2011/0150911 A1 | 6/2011 | Choo |
| 2011/0171713 A1 | 7/2011 | Bluchel et al. |
| 2011/0184377 A1 | 7/2011 | Ward et al. |

(56) References Cited

U.S. PATENT DOCUMENTS

| | | |
|---|---|---|
| 2011/0224645 A1 | 9/2011 | Winqvist et al. |
| 2012/0040429 A1 | 2/2012 | Federspiel et al. |
| 2012/0097613 A1 | 4/2012 | Hoshino |
| 2012/0219561 A1 | 8/2012 | Alt et al. |
| 2012/0244557 A1 | 9/2012 | Yu et al. |
| 2012/0305482 A1 | 12/2012 | McCrea et al. |
| 2013/0102948 A1 | 4/2013 | Reich et al. |
| 2013/0131423 A1 | 5/2013 | Wang et al. |
| 2014/0012097 A1 | 1/2014 | McCrea et al. |
| 2014/0074007 A1 | 3/2014 | McNeil |
| 2014/0131276 A1 | 5/2014 | Larm et al. |
| 2014/0231357 A1 | 8/2014 | Ward et al. |
| 2015/0111849 A1 | 4/2015 | McCrea et al. |
| 2015/0260715 A1 | 9/2015 | Hu et al. |
| 2015/0374898 A1 | 12/2015 | Fujieda |
| 2016/0003858 A1 | 1/2016 | McKendry et al. |
| 2016/0022898 A1 | 1/2016 | Larm et al. |
| 2016/0082177 A1 | 3/2016 | Ward et al. |
| 2016/0084835 A1 | 3/2016 | Ward et al. |
| 2016/0101229 A1 | 4/2016 | McCrea et al. |
| 2016/0214935 A1 | 7/2016 | Hutchinson et al. |
| 2016/0243525 A1 | 8/2016 | Song et al. |
| 2016/0331886 A1 | 11/2016 | Ward et al. |
| 2017/0035956 A1 | 2/2017 | McCrea et al. |
| 2017/0073727 A1 | 3/2017 | Ward et al. |
| 2017/0252502 A1 | 9/2017 | Ward et al. |
| 2017/0340803 A1 | 11/2017 | Larm et al. |
| 2018/0117237 A1 | 5/2018 | Brugger et al. |
| 2018/0361050 A1 | 12/2018 | Ward et al. |
| 2019/0038826 A1 | 2/2019 | McCrea et al. |
| 2019/0143027 A1 | 5/2019 | Larm et al. |
| 2020/0023001 A1 | 1/2020 | Ebong et al. |
| 2020/0056221 A1 | 2/2020 | Ward et al. |
| 2020/0171233 A1 | 6/2020 | McCrea et al. |
| 2020/0297913 A1 | 9/2020 | Larm et al. |
| 2020/0338256 A1 | 10/2020 | Ward et al. |
| 2022/0072038 A1 | 3/2022 | Ward et al. |

FOREIGN PATENT DOCUMENTS

| | | |
|---|---|---|
| CN | 101784294 A | 7/2010 |
| CN | 102740859 A | 10/2012 |
| CN | 102791307 | 11/2012 |
| CN | 106255520 A | 12/2016 |
| CN | 206345699 U | 7/2017 |
| DE | 4217917 A1 | 12/1993 |
| EP | 0306617 A | 3/1989 |
| EP | 0321703 A | 6/1989 |
| EP | 0533946 A1 | 3/1993 |
| EP | 0616845 A | 9/1994 |
| EP | 0810027 A | 12/1997 |
| EP | 1044696 A2 | 10/2000 |
| EP | 1057529 A | 12/2000 |
| EP | 1110602 A | 6/2001 |
| EP | 1219639 A | 7/2002 |
| EP | 2087916 A1 | 8/2009 |
| EP | 2556849 A1 | 2/2013 |
| GB | 2172812 A | 10/1986 |
| JP | 54-127493 U | 9/1979 |
| JP | 58-053757 A | 3/1983 |
| JP | 58-146354 A | 8/1983 |
| JP | 4-89500 A | 3/1992 |
| JP | 6040926 A | 2/1994 |
| JP | 6-505248 A | 6/1994 |
| JP | 7-178161 A | 7/1995 |
| JP | 96-510166 A | 10/1996 |
| JP | 11-502703 A | 3/1999 |
| JP | 2000-086688 A | 3/2000 |
| JP | 2000-217575 A | 8/2000 |
| JP | 2000-515543 A | 11/2000 |
| JP | 2001-190273 A | 7/2001 |
| JP | 2002-505101 A | 2/2002 |
| JP | 2002-509518 A | 3/2002 |
| JP | 2003-128502 A | 5/2003 |
| JP | 2003-520048 A | 7/2003 |
| JP | 2005-514127 A | 5/2005 |
| JP | 2005-519744 A | 7/2005 |
| JP | 2005-532130 A | 10/2005 |
| JP | 2009-521413 A | 6/2009 |
| JP | 2010-518046 A | 5/2010 |
| JP | 2010-530288 A | 9/2010 |
| JP | 2011-509083 A | 3/2011 |
| JP | 2012-501708 A | 1/2012 |
| JP | 2013-512078 A | 4/2013 |
| JP | 2014-500735 A | 1/2014 |
| JP | 2014-523914 A | 9/2014 |
| KR | 10-2008-0077405 A | 8/2008 |
| WO | 91/04086 A | 4/1991 |
| WO | 92/14361 A1 | 9/1992 |
| WO | 94/26399 A1 | 11/1994 |
| WO | 95/05400 | 2/1995 |
| WO | 96/29083 A1 | 9/1996 |
| WO | 96/40857 A1 | 12/1996 |
| WO | 97/35660 A1 | 10/1997 |
| WO | 98/05341 A1 | 2/1998 |
| WO | 98/29727 A2 | 7/1998 |
| WO | 99/06086 A1 | 2/1999 |
| WO | 99/45104 A3 | 11/1999 |
| WO | 00/23792 | 4/2000 |
| WO | 00/038763 | 7/2000 |
| WO | 00/66260 A | 11/2000 |
| WO | 01/18060 A | 3/2001 |
| WO | 01/53525 A2 | 7/2001 |
| WO | 02/060512 | 8/2002 |
| WO | 03/033143 A1 | 4/2003 |
| WO | 2003/057356 A2 | 7/2003 |
| WO | 2003/078023 A1 | 9/2003 |
| WO | 2004/008138 A2 | 1/2004 |
| WO | 2004/009798 A2 | 1/2004 |
| WO | 2005/021799 A2 | 3/2005 |
| WO | 2006/012885 A1 | 2/2006 |
| WO | 2007/058592 A1 | 5/2007 |
| WO | 2007/069983 A1 | 6/2007 |
| WO | 2007/101064 A2 | 9/2007 |
| WO | 2007/146162 A2 | 12/2007 |
| WO | 2008/095905 A2 | 8/2008 |
| WO | 2008/157570 A2 | 12/2008 |
| WO | 2009/086343 A2 | 7/2009 |
| WO | 2009/121959 A1 | 10/2009 |
| WO | 2010/029317 A2 | 3/2010 |
| WO | 2011/068897 A1 | 6/2011 |
| WO | 2011/100354 A1 | 8/2011 |
| WO | 2012/051595 A1 | 4/2012 |
| WO | 2012/112724 A1 | 8/2012 |
| WO | 2012/172341 A2 | 12/2012 |
| WO | 2013/012924 A2 | 1/2013 |
| WO | 2013/188073 A1 | 12/2013 |
| WO | 2014/209782 A1 | 12/2014 |
| WO | 2015/069942 A1 | 5/2015 |
| WO | 2015/164198 A1 | 10/2015 |
| WO | 2017/001357 A1 | 1/2017 |
| WO | 2017/151797 A1 | 9/2017 |
| WO | 2020/231830 A1 | 11/2020 |
| WO | 2021/119195 A1 | 6/2021 |
| WO | 2021/119197 A1 | 6/2021 |
| WO | 2022/216510 A1 | 10/2022 |

OTHER PUBLICATIONS

Alarabi, A. et al., "Treatment of pruritus in cholestatic jaundice by bilirubin- and bile acid-adsorbing resin column plasma perfusion," Scandinavian Journal of Gastroenterology, 27(3):223-6, 1992.

Alfaro et al., "Interleukin-8 in cancer pathogenesis, treatment and follow-up," Cancer Treat Rev., Nov. 2017, vol. 60:24-31 (abstract only).

Andrade-Gordon, P. et al., "Interaction of heparin with plasminogen activators and plasminogen: effects on the activation of plasminogen," Biochemistry, 25(14):4033-4040, 1986.

Andreasen, P.A. et al., "The plasminogen activation system in tumor growth, invasion, and metastasis," Cellular and Molecular Life Sciences, 57(1):25-40, 2000.

(56) References Cited

OTHER PUBLICATIONS

Ascencio, F. et al., "Affinity of the gastric pathogen Heficobacter py/ori for the N-sulphated glycosaminoglycan heparan sulphate," J. Med. Microbiol., 38:240-244, 1993.
Axelsson, J. et al., "Cytokines in blood from septic patients interact with surface-immobilized heparin," ASAIO Journal, 56:48-51, 2010.
Bartlett, A. and P. Park, "Proteoglycans in host-pathogen interactions: molecular mechanisms and therapeutic implications," Expert Rev. Mol. Med., 12(e5):1-33, 2015.
Bhakdi, S. and Tranum-Jensen, J., "Alpha-toxin of *Staphylococcus aureus*," Microbiological Reviews, 55(4):733-751, 1991.
Bindslev et al., "Treatment of acute respiratory failure by extracorporeal carbon dioxide elimination performed with a surface heparinized artificial lung," Anesthesiology, 67(1):117-120, 1987.
Bjorklund et al., Abstract of "Synthesis of silica-based heparin-affinity adsorbents," J. Chrom. A., 728(1-2):149-169, 1996.
Brat, D. et al., "The role of interleukin-8 and its receptors in gliomagenesis and tumoral angiogenesis," Neuro-oncology, 7(2):122-133, 2005.
Celik, T. et al., "Treatment of lyme neuroborreliosis with plasmapheresis," J. Clinical Apheresis, 31:476-478, 2016.
Chase, H., "Affinity separations utilising immobilised monoclonal antibodies—a new tool for the biochemical engineer," Chemical Engineering Science, 39(7-8):1099-1125, 1984.
Chen et al., "Microbial subversion of heparin sulfate proteoglycans," Mol. Cells, 26:415-426, 2008.
Choong, P.F. et al., "Urokinase plasminogen activator system: a multifunctional role in tumor progression and metastasis," Clinical Orthopaedics and Related Research, 415(Suppl):S46-58, 2003.
Cutler, R. et al., "Extracorporeal removal of drugs and poisons by hemodialysis and hemoperfusion," Ann. Rev. Pharmacol. Toxicol., 27:169-91, 1987.
Dixon et al., "Anthrax," New England Journal of Medicine, 341(11):815-826, 1999.
Dubreuil et al., "Effect of heparin binding on Helicobacter pylori resistance to serum," J. Med. Micro., 53:9-12, 2004.
Era, K. et al., "Development of Systems for Passive and Active CAVH," J. Japanese Society for Dialysis Therapy, 19(2):175-181, 1986.
Francy, D. et al., "Comparison of filters for concentrating microbial indicators and pathogens in lake water samples," Applied and Environmental Microbiology, 79(4):1342-52, 2012.
Frick, I. et al., "Interactions between M proteins of *Streptococcus pyogenes* and glycosaminoglycans promote bacterial adhesion to host cells," Eur. J. Biochem, 270(10):2303-11, 2003.
Fujita, M. et al., "Adsorption of inflammatory cytokines using a heparin-coated extracorporeal circuit," Artificial Organs, 26(12):1020-1025, 2002.
Garg, L. et al., "Isolation and separation of HMG proteins and histones H1 and H5 and core histones by column chromatography on phosphocellulose," Protein Expression and Purification, 14(2):155-159, 1998.
GE Healthcare, "Size exclusion chromatography cols. and resins, Selection guide," 2010, retrieved online at <<https://cdn.gelifesciences.com/dmm3bwsv3/AssetStream.aspx?mediaformatid=10061&destinationid=10016&assetid=13947>> on Jun. 27, 2019, 10 pages.
Ghannoum, M. et al., "Extracorporeal treatment for carbamazepine poisoning: Systematic review and recommendations from the EXTRIP workgroup," Clinical Toxicology, 52:993-1004, 2014.
Haase et al., "The effect of three different miniaturized blood purification devices on plasma cytokine concentration in an ex vivo model of endotoxinemia," Int. J. Artif. Organs, 31(8):722-729, 2008.
Hirmo, S. et al., "Sialyglycoconjugate- and proteoglycan-binding microbial lectins," Institute of Medical Microbiology, University of Lund, (Online). Retrieved Oct. 19, 1997 (Retrieved on Mar. 16, 2004). Retrieved from the Internet: <URL: http//www.plab.ku.dk/tcbh/Lectins12/Hirmo/paper.htm>.

Hsu, C. et al., "Early hemoperfusion may improve survival of severely paraquat-poisoned patients," PLoS ONE, 7(10):e48397, 2012.
International Preliminary Report on Patentability, dated Aug. 21, 2013, PCT Application No. PCT/US2012/025316; 8 pages.
International Search Report; PCT/SE2006/001421 dated Mar. 30, 2007.
International Search Report; PCT/US2010/058596 dated Mar. 29, 2011.
International Search Report; PCT/US2011/024229 dated May 30, 2011.
International Search Report; PCT/US2012/025316 dated May 23, 2012.
International Search Report; PCT/US2013/042377 dated Sep. 9, 2013.
International Search Report; PCT/US2014/043358 dated Dec. 1, 2014.
International Search Report; PCT/US2014/064419 dated Feb. 12, 2015.
International Search Report; PCT/US2015/026340 dated Jul. 28, 2015.
International Search Report; PCT/US2015/051239 dated Dec. 17, 2015.
International Search Report; PCT/US2016/057121 dated Dec. 30, 2016.
International Search Report; PCT/US2017/020243 dated May 19, 2017.
International Search Report; PCT/US2017/058536; dated Jan. 17, 2018.
International Search Report; PCT/US2020/032150; dated Jul. 24, 2020.
Kenig, M. et al., "Identification of the heparin-binding domain of TNF-alpha and its use for efficient TNF-alpha purification by heparin-Sepharose affinity chromatography," J. Chromatography B, 867:119-125, 2008.
Keuren et al., "Thrombogenecity of polysaccharide-coated surfaces," Biomaterials, 24:1917-24, 2003.
Kim et al., "Role of the heparin in regulating a transcapillary exchange in far north conditions," Bulletin of the Siberian Branch of the Russian Academy of Medical Sciences, 2(108), 2003.
Kishimoto, S. et al., "Human stem cell factor (SCF) is a heparin-binding cytokine," J. Biochem., 145(3):275-278, 2009.
Kumari, N. et al., "Role of interleukin-6 in cancer progression and therapeutic resistance," Tumour Biol., Sep. 2016, vol. 37(9), pp. 11553-11572 (abstract only).
Larm et al., "A new non-thrombogenic surface prepared by selective covalent binding of heparin via a modified reducing terminal residue," Biomater Med Devices Artif Organs, 11(2&3):161-173, 1983.
Lemaire, M. et al., "Treatment of paediatric vancomycin intoxication: a case report and review of the literature," NDT Plus, 3:260-264, 2010.
Lian, S. et al., "Elevated expression of growth-regulated oncogene-alpha in tumor and stromal cells predicts unfavorable prognosis in pancreatic cancer," Medicine, Jul. 2016, 95(30), pp. 1-8.
Lopatkin et al., "Efferent methods in medicine, M.," Medicine, pp. 266, 272-273, 276-279, 1989.
Low, R. et al., "Protein n, a primosomal DNA replication protein of *Escherichia coli*," Journal of Biological Chemistry, 257(11):6242-6250, 1982.
Mandal, "Sialic acid binding lectins," Experientia, 46:433-439, 1990.
Mariano et al., "Tailoring high-cut-off membranes and feasible application in sepsis-associated acute renal failure: in vitro studies," Nephrol Dial Transplant, 20:1116-1126, 2005.
Mattsby-Baltzer, I. et al., "Affinity apheresis for treatment of bacteremia caused by *Staphylococcus aureus* and/or methicillin-resistant *S. aureus* (MRSA)," J. Microbiol. Biotechnol., 21(6):659-664, 2011.
McGuigan et al., "Vancomycin (Vanocin)," Clinical Toxicology Review, 24(2):1-2, 2001.

(56) References Cited

OTHER PUBLICATIONS

Miao, J. et al., "Adsorption of doxorubicin on poly (methyl methacrylate)—chitosan-heparin coated activated carbon beads," Langmuir, 28(9):4396-4403, 2012.

Millen, H. et al., "Glass wool filters for concentrating waterborne viruses and agricultural zoonotic pathogens," J. Vis. Exp., 61:e3930, 2012.

Murphy, J.W. et al., "Structural and functional basis of CXCL 12 (stromal cell-derived factor-1 a) binding to heparin," Journal of Biological Chemistry, 282(13):10018-10027, 2007.

Nadkarni et al., Abstract of "Directional immobilization of heparin onto beaded supports," Anal. Biochem., 222(1):59-67, 1994.

Ofek et al., "Mannose binding and epithelial cell adherence of *Escherichia coli*," Infection and Immunity, 22(1):247-254, 1978.

Office Action dated Jun. 23, 2020 in Japanese Patent Application No. 2017-515161, with English translation, retrieved from <https://globaldossier.uspto.gov/#/details/JP/2017515161/A/129021> on Aug. 13, 2020.

Park, P. et al., "Activation of Syndecan-1 ectodomain shedding by *Staphylococcus aureus* α-toxin and β-toxin," J. Biol. Chem., 279(1):251-258, 2004.

Popova et al., "Acceleration of epithelial cell syndecan-1 shedding by anthrax hemolytic virulence factors," BMC Microbiolgy, 6:8, pp. 1-16, 2006.

Rauvala, H. et al., "Isolation and some characteristics of an adhesive factor of brain that enhances neurite outgrowth in central neurons," Journal of Biological Chemistry, 262(34):16625-16635, 1987.

Rauvala, H. et al., "The adhesive and neurite-promoting molecule p30: Analysis of the amino-terminal sequence and production of antipeptide antibodies that detect p30 at the surface of neuroblastoma cells and of brain neurons," Journal of Cell Biology, 107(6, 1):2293-2305, 1988.

Riesenfeld et al., "Quantitative analysis of N-sulfated, N-acetylated, and unsubstituted glucosamine amino groups in heparin and related polysaccharides," Anal Biochem, 188:383-389, 1990.

Rosenbaum, J. et al., "Effect of hemoperfusion on clearance of Gentamicin, Cephalothin, and Clindamycin from plasma of normal dogs," Journal of Infectious Diseases, 136(6):801-804, 1977.

Sagnella et al., "Chitosan based surfactant polymers designed to improve blood compatibility on biomaterials," Colloids and Surfaces B: Biointerfaces, 42:147-155, 2005.

Salek-Ardakani, S. et al., "Heparin and heparan sulfate bind interleukin-10 and modulate its activity," Blood, 96:1879-1888, 2000.

Salmivirta, M. et al., "Neurite growth-promoting protein (Amphoterin, p30) binds syndecan," Experimental Cell Research, 200:444-451, 1992.

Sanaka, T. et al., "Continuous Arteriovenous Hemofiltration," Artificial Organs, 14(5):1822-1830, 1985.

Sanchez, J. et al., "Control of contact activation on end-point immobilized heparin: The role of antithrombin and the specific antithrombin-binding sequence," J. Bio. Mat. Res., 29:665-661, 1995.

Sasaki et al., Abstract: "Improved method for the immobilization of heparin," J. Chrom., 400:123-32, 1987.

Sato, T. et al., "Experimental study of extracorporeal perfusion for septic shock," Asaio Journal, 39(3):M790-M793, 1993.

Schefold et al., "A novel selective extracorporeal intervention in sepsis: immunoadsorption of endotoxin, interleukin 6, and complement-activating product 5A," Shock, 28(4):418-425, 2007.

Sharon, "Bacterial lectins, cell-cell recognition and infectious disease," FEBS letters, 217(2):145-157, 1987.

Smorenburg, S.M. et al., "The complex effects of heparins on cancer progression and metastasis in experimental studies," Pharmacological Reviews, 53(1):93-106, 2001.

Swartz, "Recognition and management of anthrax—an update," New Engl. J. Med., 345(22):1621-1626, 2001.

Thomas et al., "Common oligosaccharide moieties inhibit the adherence of typical and atypical respiratory pathogens," Journal of Microbiology, 53:833-840, 2004.

Tonnaer, E. et al., "Involvement of glycosaminoglycans in the attachment of pneumococci to nasopharyngeal epithelial cells," Microbes and Infection, 8:316-322, 2006, available online Sep. 16, 2005.

Utt, M. et al., "Identification of heparan sulphate binding surface proteins of Helicobacter pylori: inhibition of heparan sulphate binding with sulphated carbohydrate polymers," J. Med. Microbiol., 46:541-546, 1997.

Wadstrom, T. and A. Ljungh, "Glycosaminoglycan-binding microbial proteins in tissue adhesion and invasion: key events in microbial pathogenicity," J. Med. Microbiol., 48(3):223-233, 1999.

Wang, H. et al., "HMG-1 as a late mediator of endotoxin lethality in mice," Science, 285:248-251, 1999.

Ward et al., "Specificity of adsorption in a prototype whole blood affinity therapy device for removal of *Staphylococcus aureus*," Society for Biomaterials 2013 Annual Meeting and Exposition, Apr. 10, 2013, p. 1.

Waugh D. and Wilson, C., "The interleukin-8 pathway in cancer," Clin. Cancer Res., 14(21):6735-41, 2008.

Webb, L. et al., "Binding to heparan sulfate or heparin enhances neutrophil responses to interleukin 8," PNAS USA, 90:7158-62, 1993.

Weber et al., "Development of specific adsorbents for human tumor necrosis factor-α: influence of antibody immobilization on performance and biocompatibility," Biomacromolecules, 6:1864•1870, 2005.

Weir, D., "Carbohydrates as recognition molecules in infection and immunity," FEMS Microbiology Immunology, 47:331-340, 1989.

Wendel et al., "Coating-techniques to improve the hemocompatibility of artificial devices used for extracorporeal circulation," European Journal of Cardio-thoracic Surgery, 16:342-350, 1999.

Yu, J. et al., "Adhesion of coagulase-negative staphylococci and adsorption of plasma proteins to heparinized polymer surfaces," Biomaterials, 15(10):805-814, 1994.

Zhou et al., Abstract: "Heparin-agarose aqueous ethanol suspension," J. Mol. Bio., 271(3):12, 1997.

International Search Report; PCT/US2020/064112; dated Mar. 10, 2021.

International Search Report; PCT/US2020/064110; dated Apr. 13, 2021.

International Search Report; PCT/US2022/022748; dated Aug. 17, 2022.

Ok, S. et al., "Emodin inhibits invasion and migration of prostate and lung cancer cells by downregulating the expression of chemokine receptor CXCR4," Immunopharmacology and Immunotoxicology, 34(5):768-778, 2012.

Slama, T., "Review: Gram-negative antibiotic resistance: there is a price to pay," Critical Care, 12(Suppl. 4):S4 (doi:10.1186/ccXXXX), May 21, 2008.

Stevens, K. et al., "Hydrophilic surface coatings with embedded biocidal silver nanoparticles and sodium heparin for central venous catheters," Biomaterials, 32(5):1264-1269, 2011.

\* cited by examiner

METHOD FOR TREATING DRUG INTOXICATION

CROSS-REFERENCE TO RELATED APPLICATIONS

The present application is a continuation-in-part application of U.S. patent application Ser. No. 15/446,822 filed Mar. 1, 2017, now U.S. Pat. No. 10,786,615, which application claims priority to U.S. Application No. 62/302,329, filed Mar. 2, 2016, the disclosures of which are hereby incorporated by reference in their entireties for all purposes.

BACKGROUND

Intentional and unintentional drug intoxication or drug overdose are significant causes of human and animal mortality and morbidity worldwide. Existing treatments for drug intoxication include decontamination procedures using, for example, charcoal, ipecac, or other emetics. These decontamination therapy options, though, can be accompanied by undesired side effects that include decreased intestinal motility and airway throughput. Other treatment options include the use of specific antidotes, or devices such as those of hemodialysis or hemofiltration. However, the ability of hemodialysis and hemofiltration to remove a poisoning drug and enhance the outcome for a subject is unclear.

When excess drug is allowed to be metabolized or otherwise secreted from the body without the application of any intervening therapies, a significant risk of organ damage exists. Similarly, if an intervening treatment such as hemofiltration is applied, but that treatment is relatively slow in removing the excess drug, the increased potential for harmful, or even fatal, complications remains.

Hemoperfusion provides one alternative to hemofiltration. In this extracorporeal technique, blood typically travels from a patient to a machine in which the blood perfuses a filter composed of microporous activated carbon. The small molecules to be removed from the blood become trapped in the microporous material, while blood cells continue to flow through the machine relatively undamaged. Challenges exist with this technique, however, in that the activated carbon can produce debris that becomes entrained with the effluent returning to the patient. This debris can produce blockages in the vasculature of the patient. Additionally, the perfusion process can trigger a coagulation response, as a clotting cascade can be activated within the blood of the patient.

It is apparent that there exists then a need in the art for effective and safe treatments that remove excess drug from a subject at a fast rate and/or a high degree of removal. The devices and methods described herein address this need by providing an alternate therapy characterized by potential advantages.

BRIEF SUMMARY

In general, provided herein are methods and devices for the treatment of drug intoxication or drug overdose in a subject suffering from these conditions. A sample obtained from the subject and contaminated with an excess of one or more target drugs is contacted with an adsorption media. The adsorption media comprises structures and materials that are conducive to forming adhering complexes with at least a portion of the target drug present in the sample.

In one embodiment, the disclosure provides a method for treating drug intoxication or removing a toxin in a subject in need thereof, said method comprising:

contacting a sample from a subject suffering from drug intoxication or other intoxication with an adsorption media comprising a combination of activated carbon and a substrate having at least one polysaccharide adsorbent to form a cleansed sample; and infusing the cleansed sample into the subject.

The adsorption media can comprise a combination of activated carbon and heparin. The heparin is useful both as an anticoagulant compound, increasing the safety of the treatment, and as a source of drug binding sites, increasing the efficacy of the treatment. The sample is subsequently separated from the adsorption media such that the concentration of drug in the now cleansed sample is reduced. This cleansed sample is then returned to the subject by reinfusion.

One provided method comprises contacting a sample from a subject suffering from drug intoxication with an adsorption media to form a cleansed sample. The method further comprises reinfusing the cleansed sample into the subject.

In some embodiments, the adsorption media and the drug form an adhering complex.

In some embodiments, the method further comprises separating the resulting sample from the adhering complex to produce a cleansed sample with a reduced amount of drug.

In some embodiments, the drug is a member selected from the group of analgesics, sedatives, hypnotics, antipsychotics, antidepressants, cardiovascular drugs, antihistamines, topical preparations, cold and cough preparations, stimulants, recreational drugs, street drugs, antibiotics, antimicrobials, hormones, hormone antagonists, anticonvulsants, gastrointestinal preparations, dietary supplements, or herbals.

In some embodiments, the drug is an antibiotic.

In some embodiments, the antibiotic is a member selected from the group consisting of ceftazidime, daptomycin, fosfomycin, linezolid, and vancomycin.

In some embodiments, the antibiotic is vancomycin.

In some embodiments, the drug is carbamazepine.

In some embodiments, the sample is a member selected from the group consisting of whole blood, serum, or plasma.

In some embodiments, the sample is whole blood.

In some embodiments, the adsorption media is a solid substrate having at least one polysaccharide adsorbent.

In some embodiments, the at least one polysaccharide adsorbent is a member selected from the group consisting of heparin, heparan sulfate, hyaluronic acid, sialic acid, carbohydrates with mannose sequences, chitosan, or a combination thereof.

In some embodiments, the at least one polysaccharide adsorbent is heparin.

In some embodiments, the solid substrate comprises a plurality of rigid polymer beads.

In some embodiments, the rigid polymer beads are selected from the group consisting of polyurethane, polymethylmethacrylate, polyethylene or co-polymers of ethylene and other monomers, polyethylene imine, polypropylene, or polyisobutylene.

In some embodiments, the solid substrate comprises one or a plurality of hollow or solid individual fibers.

In some embodiments, the cleansed sample has a drug content that is reduced by about 10% to about 100% from the sample using the adsorption media.

In some embodiments, the drug intoxication is the result of a drug overdose.

In some embodiments, the method occurs within a time period between 1 to 10 hours or 1 to 24 hours or 10 to 24 hours after the drug overdose by a subject, such as a human subject.

Also provided is a device for treating drug intoxication in a subject in need thereof. The device comprises a cartridge having an adsorption media disposed therein, the cartridge have a first endplate and a second endplate. The device further comprises a sample influx port to allow sample to flow into the device. The device further comprises a sample efflux port to allow sample to flow out of the device, wherein the sample flows through the first endplate, through the adsorption media, and out the sample efflux port.

In some embodiments, the adsorption media of the device is activated carbon and a solid substrate having at least one polysaccharide adsorbent on the surface thereof with a binding affinity or binding site for the drug when the sample is in contact with the adsorption media. The drug binds to binding sites on the at least one polysaccharide adsorbent and becomes separated from the sample.

In some embodiments, the at least one polysaccharide adsorbent of the device is a member selected from the group consisting of heparin, heparan sulfate, dextran sulfate, hyaluronic acid, sialic acid, carbohydrates with mannose sequences, chitosan, and a combination thereof.

In some embodiments, the at least one polysaccharide adsorbent of the device is heparin.

In some embodiments, the solid substrate of the device comprises a plurality of rigid polymer beads.

In some embodiments, the rigid polymer beads of the device are selected from the group consisting of polyurethane, polymethylmethacrylate, polyethylene or co-polymers of ethylene and other monomers, polyethylene imine, polypropylene, or polyisobutylene.

In some embodiments, the solid substrate of the device comprises one or a plurality of hollow fibers.

These and other objects, aspects and embodiments will become more apparent when read with the detailed description of the invention together with the accompanying figures.

BRIEF DESCRIPTION OF THE DRAWINGS

FIG. 3A shows reduction in concentration for ceftazidime; FIG. 3B shows reduction in concentration for daptomycin; FIG. 3C shows reduction in concentration for Fosfomycin; and FIG. 3D shows reduction in concentration for linezolid.

FIG. 4A illustrates a blood collection through absorbate. FIG. 4B shows autologous transfusion of purified blood.

FIG. 6A illustrates a measurement of total hemoglobin tHb. FIG. 6B illustrates a measurement of free hemoglobin (hemolysis). FIG. 6C illustrates a measurement of red blood cells (RBC). FIG. 6D illustrates a measurement of hematocrit (Hct). FIG. 6E illustrates a measurement of $Ca^{2+}$. FIG. 6F illustrates a measurement of blood pressure.

DETAILED DESCRIPTION

Figure 1:
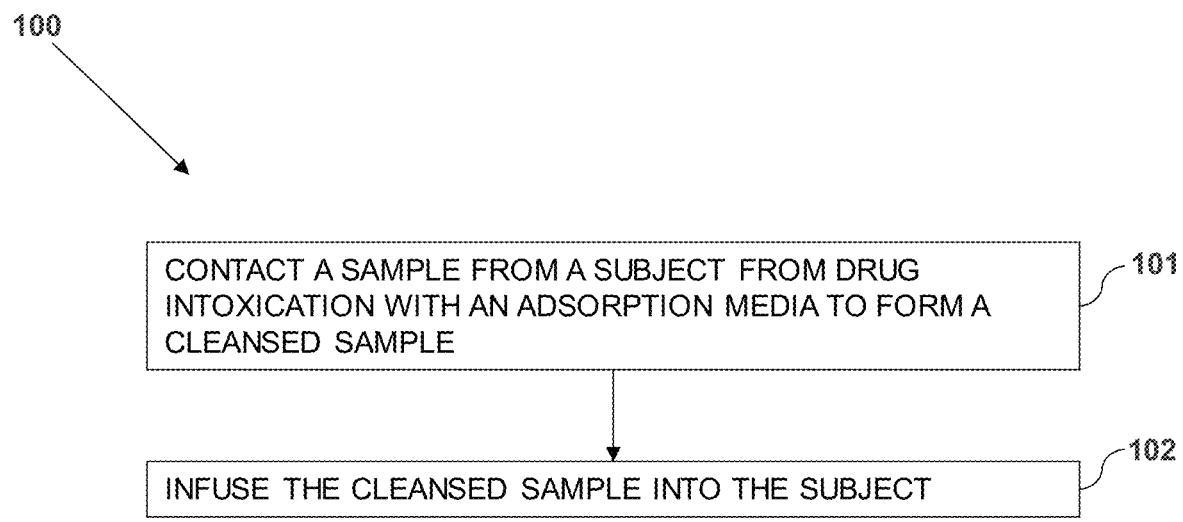
FIG. 1 is a flowchart of a process in accordance with an embodiment.

The present invention relates in part to extracorporeal devices and methods for treating drug intoxication or a drug overdose. The methods include the use of adsorption media to cleanse a sample from a subject that is suffering from drug poisoning. The cleansed sample can then be continuously or intermittently reinfused into the subject.

A technical advantage of the embodiments described herein is that the use of activated carbon and heparin as an adsorption medium increases both the safety and the efficacy of the treatment. The inventors have made the surprising discovery that in addition to binding thrombin and antithrombin III, heparin is capable of interacting with drugs such as antibiotics in a way that allows the heparin to separate drug molecules from a sample withdrawn from an overdosed subject.

I. Definitions

As used herein, the following terms have the meanings ascribed to them unless specified otherwise.

The term "extracorporeal therapy" refers to a medical procedure that is conducted outside the body. In some instances, extracorporeal therapies include methods in which a bodily fluid such as blood is taken from the individual and desired products such as, but not limited to, oxygen, blood-anticoagulants, anesthetics, and the like are added to the body fluid before it is returned to the individual. In other instances, an extracorporeal therapy includes removing undesired products such as toxins or poisons from the body or body fluids. A combination of removal and additions to the blood being treated is also possible, e.g., during routine kidney dialysis. These undesired products can be exogenous chemicals or substances naturally occurring within the body.

The term "activated carbon" also called "activated charcoal," is a form of carbon processed to have small, low-volume pores that increase the surface area available for adsorption of toxins. Activated is sometimes substituted with "active."

The term "adsorption media" refers to a material to which a cell, organism, virus, toxin, pathogen, polypeptide, polynucleotide, chemical molecule, small molecule, drug, biological molecule or fragment thereof can adhere to the surface thereof. In certain instances, a pathogen is disclosed in U.S. Pat. No. 9,173,989, incorporated herein by reference).

The term "adhering complex" refers to a complex of at least two molecules wherein the first molecule is attached (e.g., linked, coupled or bound) to the surface of a substrate and the second molecule (e.g., a drug) is attached to the first molecule. The first molecule can be the adsorbent. In certain aspects, the drug attaches to the adsorbent to form an adhering complex.

The term "high surface area" refers to the property of having a large specific surface area to volume ratio.

The term "adsorbent" refers to a solid substrate with a chemical compound, a biological molecule, or a material that is attached (e.g., linked, coupled or bound) thereto. In certain instances, the adsorbent is the solid substrate itself. In one embodiment, an adsorbent is a polymer resin with a polysaccharide bound thereto.

The term "rigid polymer bead" refers to a bead, granule, pellet, sphere, particle, microcapsule, sphere, microsphere, nanosphere, microbead, nanobead, microparticle, nanoparticle, and the like that is made from a polymer resin or other biocompatible substrate material.

The term "carbohydrate" refers to a molecule containing carbon, hydrogen and oxygen atoms, and usually with the empirical formula $C_x(H_2O)_y$, where x and y are different numbers. Examples of carbohydrates includes monosaccharides, disaccharides, oligosaccharides, and polysaccharides.

The term "polysaccharide" refers to a molecule of monosaccharide units joined together by glycosidic bonds, and having an empirical formula of $C_x(H_2O)_y$, where x is between 200 to about 3000.

The term "hydrophilic surface" includes a surface with a water contact angle less than 90° when the surface is flat.

The terms "about" and "approximately equal" are used herein to modify a numerical value and indicate a defined range around that value. If "X" is the value, "about X" or "approximately equal to X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

II. Detailed Descriptions of the Embodiments

FIG. 1 presents a flowchart of a process 100 for treating drug intoxication in a subject in need thereof, in accordance with an embodiment of the invention. In operation, a sample from a subject such as a human suffering from drug intoxication or overdose is contacted 101 with an adsorption media to form a cleansed sample. Thereafter, the cleansed sample is infused 102 into the subject.

The drug or toxic substance intoxication or overdose can be the result of either intentional or unintentional exposure. The amount of administered drug required to trigger an overdose response can be based on drug-specific parameters, and/or subject-specific parameters, such as body mass, metabolism, and allergic sensitivities. In some cases, an overdose can be the result of administration of a single drug. In other cases, an overdose involves combined drug intoxication or multiple drug intake. The effects of poisoning through drug intoxication can range from minor and easily treatable complications, to more serious effects requiring prolonged hospitalization, and to immediate and life-threatening physiological responses such as single or multi-organ failure. For example, the kidneys are particularly sensitive to damage from certain anti-microbial drugs. These include powerful antibiotics currently being used due to the increase in the frequency of drug-resistant bloodstream infections. Symptoms can include, for example, ataxia, ileus, confusion, nystagmus, seizures, dysrhythmias, cerebral edema, anaphylaxis, reduced urine output, and coma. In many cases, the severity of the poisoning effect can be mitigated by rapid, safe and effective elimination of the drug from the subject. The rapidity and degree of elimination can be directly related to the favorability of the treatment outcome.

The subject suffering from drug intoxication can be an animal. In some embodiments, the subject is a mammal. In some embodiments, the subject is a human. The subject can be of any gender or age. In some embodiments, the subject has overdosed with drug immediately prior to the application of the treatment method. In some embodiments, the subject has overdosed about 1 hr, about 2 hr, about 3 hr, about 4 hr, about 5 hr, about 6 hr, about 7 hr, about 8 hr, about 9 hr, about 10 hr, about 11 hr, about 12 hr, about 13 hr, about 14 hr, about 15 hr, about 16 hr, about 17 hr, about 18 hr, about 19 hr, about 20 hr, about 21 hr, about 22 hr, about 23 hr, about 24 hr, about 25 hr, about 30 hr, about 35 hr, about 40 hr, about 45 hr, about 50 hr, about 55 hr, about 60 hr, about 65 hr, about 70 hr, or about 75 hr prior to the application of the treatment method. In some embodiments, the method occurs within 10 hr to 24 hr after the subject has overdosed.

The sample from the subject can be any bodily fluid taken from the subject. In some embodiments, the sample comprises whole blood. In some embodiments, the sample comprises serum. In some embodiments, the sample comprises plasma. In some embodiments, the sample comprises cerebrospinal fluid. The sample can be taken from the subject in the form of a discrete sample to be treated with the method. The sample can be taken from the subject in the form a continuous or semi-continuous stream. The amount of sample that can be used in the claimed methods is not intended to be limited. It can range from less than 1 mL to above 1 L, up to and including the entire blood volume of the subject when the sample comprises blood and when continuous recirculation back to the subject is employed. One or more 'passes' through the adsorption bed may be used if needed.

In some embodiments, the sample is taken from the subject at a rate of about 5 mL/min, about 10 mL/min, about 15 mL/min, about 20 mL/min, about 25 mL/min, about 30 mL/min, about 35 mL/min, about 40 mL/min, about 45 mL/min, about 50 mL/min, about 60 mL/min, about 70 mL/min, about 80 mL/min, about 90 mL/min, about 100 mL/min, about 150 mL/min, about 200 mL/min, about 250 mL/min, about 300 mL/min, about 350 mL/min, about 400 mL/min, about 450 mL/min, about 500 mL/min, about 550 mL/min, about 600 mL/min, about 700 mL/min, about 800 mL/min, about 900 mL/min, about 1000 mL/min, or even about 2000 to 6000 mL/min.

The adsorption media for cleansing the sample can be a microporous media such as activated carbon or size exclusion chromatography resin that has been rendered blood compatible. In some embodiments, the preferred adsorption media does not contain activated carbon. The adsorption media can be coated with at least one affinity ligand such as heparin, heparan sulfate, mannose, dextrose, dextran sulfate, other carbohydrates, antibodies, and other adhesins, such as opsonins. By including heparin ligands with other non-heparin affinity ligands, the blood compatibility of the device is improved and the broad spectrum characteristics of adsorption are increased. The adsorption media can be in a vessel such as a column, cartridge, tube, centrifuge tube, bottle, flexible bag, and the like, or any vessel wherein the cleansed sample can be removed without disturbing the drug attached to the media.

Heparin is one of the most commonly used drugs in clinical medicine. Heparin and its low molecular weight derivatives, commonly referred to as low molecular weight (LMW) heparins, are commonly used as anticoagulants during extracorporeal procedures such as cardiopulmonary bypass, extracorporeal membrane oxygenation, dialysis, plasmapheresis, and hemoperfusion. For example, undesired products like naturally occurring toxins or poisons can be also removed from body fluids with specific types of extracorporeal circuits. Adsorption on activated carbon has been used to remove blood-borne poisons, such as pathogens and cytokines as described in PCT Publication No.: WO 2011068897 A9, incorporated herein by reference.

Heparin is a polysaccharide that can be isolated from mammalian tissue. It has a specific expression in the basophilic granules of mast cells in mammalian tissue. Since 1916, heparin has been recognized for its ability to prevent blood from clotting, and for its relatively short half-life in the body. Systemic heparin, administered by injection of the free drug, has been used clinically for more than 50 years as a safe and effective blood anticoagulant and antithrombotic agent. The effects of heparin on blood coagulation or clotting diminish fairly quickly after administration is halted, making its use during surgery and other procedures effective and safe. For example, heparin's anticoagulant and antithrombogenic properties are useful during many medical procedures to minimize undesirable interactions between blood and the man-made surfaces of extracorporeal circuits. Once the procedure is over, the administration of heparin may be terminated. The heparin concentration in the patient's blood diminishes to a safe level within a few hours because of its short half-life in the body.

Heparin exerts its anticoagulant activity primarily through high affinity binding and activation to the serine protease inhibitor, antithrombin (AT). Binding is mediated by a specific pentasaccharide sequence. AT, an important physiological inhibitor of blood clotting, neutralizes activated clotting factors by forming stable complexes with these factors. Heparin binding causes AT to undergo steric changes that dramatically increase the rate of inhibition of clotting factors, thereby attenuating blood clotting and thrombus formation.

In addition to its well established and continuing use in the treatment of thromboembolic disorders and the prevention of surface-induced thrombogenesis, heparin has been found to have a wide range of other functions unrelated to its function as an anticoagulant. For example, a large number of proteins in blood can bind to heparin and/or the closely-related polysaccharide heparan sulfate with high affinity. Some examples are antithrombin (AT), fibronectin, vitronectin, growth factors (e.g. the fibroblast growth factors, the insulin like growth factors, etc.). Human serum albumin (HSA) also binds to heparin, but with a lower affinity despite its high concentration in blood.

Others have considered utilizing the selective adsorption properties of systemic, free heparin for hindering infections, by introducing heparin fragments and/or so-called sialic-containing fragments directly into the vascular system. Although this approach has been investigated by many scientists, only limited success has been reported to date. A common problem has been bleeding complications associated with the large amounts of free heparin introduced into the blood stream, e.g., by injection, to achieve a clinically-useful reduction of drug intoxication. The present invention does not require the use of any free, systemic heparin for efficacy, and thus may eliminate bleeding complications. This is accomplished by permanently binding the heparin or heparan sulphate to a solid substrate with high surface area, and exposing it to the blood within a cartridge or filter containing this adsorption media.

Various materials, in shape and composition, can be used as an adsorption media in the methods and devices. All suitable adsorbent substrates provide high surface area while promoting the conveyance of adsorbates to the adsorbent sites that bind them (primarily) by forced convective or diffusion transport. Useful solid substrates for creating the adsorption media include non-porous rigid beads, particles or packing, reticulated foams, a rigid monolithic bed (e.g. formed from sintered beads or particles), a column packed with woven or non-woven fabric, a column packed with a yarn or solid or hollow mesoporous or microporous monofilament fibers, a spiral wound cartridge formed from flat film or dense membrane, or a combination of media such as a mixed bead/fabric cartridge. In some embodiments, the solid substrate is one that is initially mesoporous or microporous, but becomes essentially non-porous when the surface is treated before, during, or after the creation of adsorption sites.

In certain instances, the substrate includes a polymer or rigid polymer bead. The substrate can also be metal, ceramic, glass, natural mineral, silica, and the like. The substrate is preferrably a surface treated with a coat comprising a ligand so that it is effectively hidden or overcoated. Typically, the substrate does not leach impurities that cause clinically significant problems if they enter the patient's blood.

The solid substrate of the device can comprise a material having a large surface area. The total surface area of the solid substrate can be in the range of 0.1-10,000 square meters, preferably in the range of 0.5-50 square meters, such as 0.5, 1, 1, 2, 2, 5, 10, 25, 40 and 50 square meters and numerical values between these.

In some embodiments, the material of the solid substrate is selected from the group consisting of glass, silica, latex, cellulose, cellulose acetate, chitin, chitosan, cross-linked dextran, cross-linked agarose, cross linked alginate, polyethylene, polypropylene, polystyrene, polycarbonate, polysulfone, polyacrylonitrile, silicone, fluoropolymers (such as polytetrafluoroethylene), polyurethanes, and other synthetic polymers. Other materials commonly used for medical applications may also be employed. In some embodiments, the solid substrate comprises a cross-linked polysaccharide. The solid substrate can comprise a plurality of adsorbent monolayers, filters, membranes, solid fibers, hollow fibers, particles, or beads. Optionally, the solid substrate can be present in other forms or shapes providing a large surface area.

One useful approach is to create a mixed media solid substrate by layering the different media of the solid substrate in a parfait-type arrangement such that the sample contacts the different media in series or parallel flow. Certain mixed media embodiments are disclosed in U.S. Pat. No. 8,758,286, incorporated herein by reference. The mixed media can be antithrombogenic media such as heparin together with a thrombogenic media such as cationic media. For example, chitosan is a highly cationic, positively-charged carbohydrate. Other positively charged molecules, such as polyethylene imine (PEI), or chitosan can be used. These cationic media are thrombogenic.

One arrangement of the different media is to position unblended anti-coagulation media (anti-thrombogenic media such as heparin) at the fluidic entrance and/or the fluidic exit regions of the solid substrate, with an optionally blended region comprising other materials interposed between the entrance and exit regions such as a thrombogenic media (e.g. cationic media). In the case of media in fiber form, a mixed woven, knitted, or nonwoven structure can be prepared by methods well known in the textile industry to form fabric from the mixed fiber. In some embodiments, a yarn is prepared from finer multifilament yarn or monofilament made from two or more fibers with different surface chemistries, wherein one fiber type contains a surface that actively prevents blood clotting on contact. This mixed-fiber yarn can then be used to prepare fabric suitable for a sample (e.g. blood) to contact.

In some embodiments, the adsorption media provides a surface to attach a polysaccharide adsorbent that can bind a drug. In some embodiments, the adsorption media includes a solid substrate with a high surface area having at least one polysaccharide adsorbent on the surface thereof. In some embodiments, the at least one polysaccharide adsorbent is a member selected from the group consisting of heparin, heparan sulfate, hyaluronic acid, sialic acid, carbohydrates with mannose sequences, chitosan, or a combination thereof. In one instance, the adsorbent media is mannose as is disclosed in U.S. patent application Ser. No. 14/973,617, filed Dec. 17, 2015, incorporated herein by reference.

In some embodiments, the adsorption media provides a hydrophilic surface without a polysaccharide adsorbent ("a naked surface"). In some embodiments, the adsorption media includes a solid substrate with a high surface area and a hydrophilic cationic surface. In some embodiments, the adsorption media includes a solid substrate with a high surface area and a hydrophilic neutral surface.

Covalent attachment of a carbohydrate to a solid substrate provides control of parameters such as surface density and orientation of the immobilized molecules as compared to non-covalent attachment. These parameters have been shown to influence the binding of targeted drug molecules to the immobilized carbohydrate molecules. In certain aspects, the surface concentration of the carbohydrate on the solid substrate is in the range of 0.01 to about 1 $\mu g/cm^2$, such as 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.3, 0.4, 0.5, 0.6, 0.7, 0.8, 0.9 or 1 $\mu g/cm^2$.

In fact, end-point attachment is an advantageous due to a lack of steric hindrance when compared to multi-point attachment, whether or not the multi-point attachment is covalent or non-covalent. Multipoint attachment requires the (oligomeric) ligand to be roughly parallel with the substrate surface with certain repeat units blocked and therefore unavailable for binding to adsorbates. End-point attachment of the ligand exposes virtually all the potential binding sites to adsorbate (drugs).

The adsorption media can comprise an anti-coagulation component. In some embodiments, the anti-coagulation component is heparan sulfate. In some embodiments, the anti-coagulation component is heparin. The heparin of the adsorption media is capable of binding antithrombin III (ATIII), and can also be capable of binding with one or more target drugs to be eliminated or reduced from the sample. A mixed adsorption media can be useful when the targeted one or more drugs do not bind to heparin. A mixed adsorption media can also be useful when the antithrombogenic properties of heparin as well as the drug-binding properties of another adsorption media component are both desired.

In another embodiment, the present invention provides a full-length heparin as an adsorbent media (see, U.S. Pat. No. 8,663,148, incorporated herein by reference). In certain instances, the full length heparin has a mean molecular weight in the range of 15-25 kDa such as about 21 kDa. The use of full-length heparin molecules can provide an increase in the binding capacity for heparin binding entities per surface area unit as compared to other heparin surfaces that do not comprise full-length molecules. The heparin is preferably covalently linked to the solid substrate. Covalent coupling of the heparin molecules prevent leaching of heparin into the sample upon contacting with the heparin coated surface. Leaching of heparin has been a problem in prior art techniques employing, for example, electrostatic binding of heparin to surfaces, or the utilization of free heparin.

In a more specific embodiment, the heparin is linked to the solid substrate by covalent end-point attachment. Covalent end-point attachment means that the heparin is covalently attached to the solid substrate via the terminal residue of the heparin molecule.

In certain embodiments, the adsorption media comprises active carbon and at least one polysaccharide adsorbent. The at least one polysaccharide adsorbent is a member selected from the group consisting of heparin, heparan sulfate, hyaluronic acid, sialic acid, carbohydrates with mannose sequences, chitosan, and a combination thereof. In some embodiments, the adsorption media comprises active carbon, heparin and/or heparan sulfate.

Suitable heparinic anticoagulants include heparins or active fragments and fractions thereof from natural, synthetic, or biosynthetic sources. Examples of heparin and heparin substitutes include, but are not limited to, heparin calcium, such as calciparin; heparin low-molecular weight, such as enoxaparin (LOVENOX®), Bemiparin, Certoparin, Dalteparin, Nadroparin, Parnaparin, Reviparin or Tinzaparin; heparin sodium, such as heparin, lipo-hepin, liquaemin sodium, and panheprin; heparin sodium dihydroergotamine mesylate; lithium heparin; and ammonium heparin.

In addition to heparin and heparan sulfate, there are other biologically active chemical moieties including other carbohydrates that can remove harmful substances from blood and biological fluids that are not efficiently removed by immobilized heparin alone. For example, chitosan, a highly cationic, positively-charged carbohydrate will bind endotoxins. Other positively charged molecules, such as polyethylene imine (PEI), can also bind endotoxins. However, cationic surfaces are significantly less blood compatible than heparinized surfaces and can lead to increased thrombogenicity, a dangerous condition in blood contacting devices. (See Sagnella S., and Mai-Ngam K. 2005, Colloids and Surfaces B: Biointerfaces, Vol. 42, pp. 147-155, Chitosan based surfactant polymers designed to improve blood compatibility on biomaterials and Keuren J. F. W., Wielders S. J. H., Willems G. M., Morra M., Cahalan L., Cahalan 9P., and Lindhout T. 2003, Biomaterials, Vol. 24, pp. 1917-1924. Thrombogenecity of polysaccharide-coated surfaces). While it is possible to use an adsorption cartridge containing PEI, chitosan or other inherently thrombogenic surfaces as a bioactive adsorbent to remove LPS or endotoxins from blood, due to the severe clotting risk, the patient would need a high dose of systemic anticoagulant. In the case of systemic heparin, this could lead to a bleeding risk and possible thrombocytopenia. The present invention provides a method for preparing the adsorption bed from a mixture of heparinized media and media which is inherently thrombogenic. By assembling an adsorption cartridge with both heparinized surfaces and, for example, cationic surfaces (or other thrombogenic surfaces), cytokines, pathogens, and endotoxins can be safely removed from blood or biological fluid.

The use of this embodiment is based, in part, on the concept that an antithrombogenic surface in intimate contact with, or in close proximity to a thrombogenic surface can prevent clinically significant thrombus formation that would otherwise occur if the thrombogenic surface was used alone. In the case of adsorption media in the form of beads or particles, one embodiment is to blend the different adsorption media together before packing them into a cartridge or other housing. This provides increased close contact among the various surface chemistries on adjacent beads, thereby permitting efficient manufacturing of adsorption cartridges or filters. A related approach is to layer the different media in a 'parfait-type' arrangement within the housing such that the blood contacts the different media in series or parallel flow. One arrangement of the different media within a cartridge is to position unblended antithrombogenic media at the entrance and/or the exit of the cartridge, with an optionally blended region containing the more thrombogenic media interposed between the entrance and exit regions. In the case of media in fiber form, a mixed woven, knitted, or nonwoven structure can be prepared by standard methods in the field to form fabric from the mixed fiber. Alternatively a yarn can be prepared from finer multifilament yarn or monofilament made from two or more fibers with different surface chemistries, as long as one fiber type contains a surface that actively prevents blood clotting on contact. The mixed-fiber yarn can then be used to prepare fabric for blood contact.

Hollow fiber or solid fiber adsorption media can be blended and used to make cartridges that resemble hollow-fiber dialyzers or oxygenators. For membrane or film-type adsorption media of the type that is used in a spiral-wound adsorption cartridges, two or more surface chemistries may be used in close proximity to each other such that the blood must contact both surface chemistries (nearly) simultaneously. This could be done with a regular or random array of the various binding groups within the surface layer of the membrane film, or by forming a flow path for blood between two closely-spaced membrane films, one of which is anti-throbogenic.

The adsorption media can be selected to comprise sites with specific binding affinity for a drug target of interest to be eliminated or reduced from the sample. The adsorption media can be selected to comprise sites with promiscuous binding affinity that are capable of binding drugs having diverse structures. In some embodiments, the adsorption media comprises a plurality of binding site types, each with a different degree of specificity or promiscuity. In some embodiments, the adsorption media comprises a plurality of binding site types, each specific for a different drug target to be eliminated or reduced from the sample. By combining more than one adsorption media, surface chemistry, or binding site, the solid substrate is able to target a broader spectrum of drug targets. In some embodiments, all or the majority of the drug binding sites of the adsorption media are provided by heparin.

In certain instances, the adsorbent media is one or more of the following active carbon, charcoal, alumina, silica gel, zeolite, bentonite, calcium phosphate, ion-exchange resin, and chelating resin may be cited. Among other adsorption bases mentioned above, such carbonaceous materials as active carbon and charcoal which possess the ability to effect adsorption are useful. The active carbon proves particularly suitable.

Activated carbon can be used as the adsorbent and in various forms such as, for example, powder, granules, and fibers. It is nevertheless particularly favorable to use the activated carbon in the powdery or granular form. In this case, the active carbon has a particle diameter in the range of 5 μm-10 mm. The amount of the activated carbon to be incorporated into the adsorption media is in the range of 0.02-90 wt. %.

The adsorption media has high antidotal activity, and is capable of adsorbing exogenous or endogenous toxins in a patient.

In certain aspects, the activated carbon employed according to the disclosure comprise discrete activated carbon particles, such as discrete activated carbon beads. The activated carbon particles, or activated carbon beads, have mean particle diameters in the range from 0.01 to 2.0 mm, in particular 0.05 to 1.0 mm, or 0.1 to 1.0 mm. Particularly advantageously, an activated carbon is used which is particularly mechanically stable and has a bursting pressure of at least 5 Newtons, in particular a bursting pressure in the range from 5 Newtons to 20 Newtons, per activated carbon particle or activated carbon bead.

According to the disclosure, the activated carbon preferably employed has a raw density in the range from 700 to 975 g/cm$^3$, in particular 750 to 950 g/cm$^3$, preferably 800 to 900 g/cm$^3$. Furthermore, it has a total porosity of 10%-70% or 40 to 70%, in particular 45 to 65%, preferably 50 to 60%.

According to the invention, the activated carbon preferably employed has a specific total pore volume in the range from 0.1 to 2.5 cm$^3$/g, in particular 0.2 to 2.0 cm$^3$/g, preferably 0.3 to 1.5 cm$^3$/g, particularly preferably 0.4 to 1.0 cm$^3$/g. Here, the content of pores having pore diameters ≤36 Å is advantageously at least 65%, in particular at least 70%, preferably at least 75%, and can be up to 95%, in particular up to 90%.

For medicinal use, it is particularly advantageous if the activated carbon employed has a specific surface area (Brunauer-Emmett-Teller (BET) surface area) of at least 500 g/m$^2$, in particular at least 750 g/m$^2$, preferably at least 1,000 g/m$^2$, particularly preferably at least 1200 g/m$^2$. Customarily, the activated carbon employed has a specific surface area (BET surface area) in the range from 500 to 2,500 g/m$^2$, in particular 750 to 2,250 g/m$^2$, preferably 900 to 2,000 g/m$^2$, particularly preferably 1,000 to 1,750 g/m$^2$. The aforementioned BET values relate to pores having pore diameters up to 400 Å inclusive.

Other adsorbents that can be used in lieu of activated carbon or in addition to activated carbon include, hydrophobic particulate material such as cellulose coated activated carbon, carboncarbon nanotubes, hydrophobic silica, styrenic polymers, polydivinylbenzene polymers and styrene-divinylbenzene copolymers. Activated carbon can be used, for example, in particulate form as powder or fine granules less than 1.0 mm in size with an average diameter between 0.001 and 0.15 mm or as granular activated carbon with relatively larger particle size compared to powdered activated carbon. Granular activated carbon has the advantage of easier handling and higher safety with regard to its retention in the filtrate space. Activated carbon which may be used according to the invention may be acid washed granular activated carbon particles. According to one aspect of the present invention, the particle size of the granular activated carbon is in the range of from >10 mesh (2.0 mm) and <40 mesh (0.420 mm). According to another aspect of the present invention, particle size of the activated carbon is in the range of about 0.200 mm.

The total surface area of activated carbon which may be advantageously used according to the invention is in the range of from 600 m$^2$/g and 1200 m$^2$/g. Such activated carbon can be purchased, for example, as Norit. GAC 1240 PLUS A (Norit Nederland BV). Examples for polymeric hydrophobic material which can be used, are, for example, styrenic polymers like DOWEX OPTIPORE L493 and V493 or Amberlite XAD-2, polydivinylbenzene polymers or styrene-divinylbenzene copolymers (e.g. Amberlite XAD4 or Amberchrom CG161), poly(1-phenylethene-1,2-diyl) (Thermocole), or hydrophobic silica, which is silica that has hydrophobic groups chemically bonded to the surface, or combinations thereof. Hydrophobic silica can be made both from fumed and precipitated silica. Another hydrophobic material which can be used is known as Ujotit, a copolymer of styrene and divinylbenzene without any functional groups, which is available as Ujotit PA-30, Ujotit PA-40 or Ujotit PA-20.

In some embodiments, the adsorption media comprises heparin and/or heparan sulfate at a concentration of about 0.1 U/mL to about 30 U/mL. In some embodiments, the adsorption media comprises heparin and/or heparan sulfate at a concentration of about 0.1 U/mL to about 10 U/mL, about 0.5 U/mL to about 20 U/mL, about 0.75 U/mL to about 15 U/mL, about 1 U/mL to about 10 U/mL, or about 1.5 U/mL to about 5 U/mL. In some embodiments, the adsorption media comprises heparin and/or heparan sulfate at a concentration of about 0.1 U/mL, about 0.5 U/mL, about 0.8 U/mL, about 1.0 U/mL, about 1.5 U/mL, about 2 U/mL, about 5 U/mL, about 10 U/mL, about 15 U/mL, about 20 U/mL, about 25 U/mL, or about 30 U/mL.

In some embodiments, the adsorption media comprises a combination of activated carbon and heparin and/or heparan sulfate. In some embodiments, the adsorption media comprises about 0.01 wt. % to about 99.9 wt. % of activated carbon and/or charcoal and about 0.01 wt. % to about 99.9 wt. % of heparin and/or heparan sulfate. In some embodiments, the adsorption media comprises about 0.02 wt. % to about 90 wt. %, about 1 wt. % to about 20 wt. %, about 5 wt. % to about 35 wt. %, about 10 wt. % to about 50 wt. %, about 15 wt. % to about 75 wt. %, about 20 wt. % to about 95 wt. %, about 25 wt. % to about 60 wt. %, about 30 wt. % to about 60 wt. %, about 40 wt. % to about 70 wt. %, or about 50 wt. % to about 85 wt. % of activated carbon and/or charcoal. In some embodiments, the adsorption media comprises about 0.01 wt. %, about 0.02 wt. %, about 0.05 wt. %, about 1 wt. %, about 2 wt. %, about 5 wt. %, about 10 wt. %, about 15 wt. %, about 20 wt. %, about 30 wt. %, about 40 wt. %, about 50 wt. %, about 60 wt. %, about 70 wt. %, about 80 wt. %, about 90 wt. %, or about 99 wt. % of activated carbon and/or charcoal. In some embodiments, the adsorption media comprises about 0.01 wt. % to about 99.9 wt. % of heparin and/or heparan sulfate. In some embodiments, the adsorption media comprises about 0.02 wt. % to about 90 wt. %, about 1 wt. % to about 20 wt. %, about 5 wt. % to about 35 wt. %, about 10 wt. % to about 50 wt. %, about 15 wt. % to about 75 wt. %, about 20 wt. % to about 95 wt. %, about 25 wt. % to about 60 wt. %, about 30 wt. % to about 60 wt. %, about 40 wt. % to about 70 wt. %, or about 50 wt. % to about 85 wt. % of heparin and/or heparan sulfate. In some embodiments, the adsorption media comprises about 0.01 wt. %, about 0.02 wt. %, about 0.05 wt. %, about 1 wt. %, about 2 wt. %, about 5 wt. %, about 10 wt. %, about 15 wt. %, about 20 wt. %, about 30 wt. %, about 40 wt. %, about 50 wt. %, about 60 wt. %, about 70 wt. %, about 80 wt. %, about 90 wt. %, or about 99 wt. % of heparin and/or heparan sulfate.

The solid substrate can be in the form of a plurality of solid beads or particles. The beads can be made of materials that are sufficiently rigid so as to resist deformation or compaction under the encountered flow rates and pressures. In some embodiments, sufficient substrate rigidity is defined as rigidity producing no significant increase in pressure drop across an adsorption bed during about one hour of flow of water or saline at typical clinical flow rates. For example, a suitable substrate rigidity would produce a less than 10-50% increase in pressure drop relative to the initial pressure drop (e.g., measured within the first minute of flow) when measured at a similar flow rate, e.g., of saline.

The beads or other high-surface-area substrates can be made from a number of different biocompatible materials, such as metals, natural or synthetic polymers or non-polymeric material including glasses, ceramics and metals, that are essentially free of leachable impurities. Some exemplary polymers including polyurethane, polysulfone, polyacrylonitrile, polycarbonate, polymethylmethacrylate, polyethylene or co-polymers of ethylene and other monomers, polyethylene imine, polypropylene, and polyisobutylene. Examples of useful substrates include nonporous Ultra High Molecular Weight Polyethylene (UHMWPE). Other suitable bead materials are polystyrene, high density and low density polyethylene, silica, latex, glass, cellulose, crosslinked agarose, crosslinked dextran, crosslinked alginate, silicone, fluoropolymer, chitin, and chitosan. In certain instances, any non-toxic, non-leaching substrate is suitable.

The size of the solid substrate can be selected according to the volume of the sample to be treated or other parameters. In some embodiments, each bead of the plurality of rigid polymer beads has an average outer diameter of about 1 μm to about 1 mm, e.g., 1 μm, 2 μm, 3 μm, 4 μm, 5 μm, 6 μm, 7 μm, 8 μm, 9 μm, 10 μm, 15 μm, 20 μm, 25 μm, 30 μm, 35 μm, 45 μm, 55 μm, 60 μm, 65 μm, 70 μm, 75 μm, 80 μm, 85 μm, 90 μm, 95 μm, 100 μm, 200 μm, 300 μm, 400 μm, 500 μm, 600 μm, 700 μm, 800 μm, 900 μm, or 1 mm. For example, polyethylene beads from DSM Biomedical (Berkeley, CA) having an average diameter of 300 μm are suitable for the methods and devices disclosed herein. In other embodiments, each bead of the plurality of rigid polymer beads has an average diameter of about 10 μm to about 200 μm, e.g., 10 μm, 15 μm, 20 μm, 25 μm, 30 μm, 35 μm, 45 μm, 55 μm, 60 μm, 65 μm, 70 μm, 75 μm, 80 μm, 85 μm, 90 μm, 95 μm, 100 μm, 105 μm, 110 μm, 115 μm, 120 μm, 125 μm, 130 μm, 135 μm, 140 μm, 145 μm, 150 μm, 155 μm, 160 μm, 165 μm, 170 μm, 175 μm, 180 μm, 185 μm, 190 μm 195 μm, 200 μm or more. Generally, a particle size in the range of 20-200 μm such as 10, 20, 30, 40, 50, 60, 70, 80, 90, 100, 110, 120, 130, 140, 150, 160, 170, 180, 190, or 200 μm is useful, but in high flow rate applications larger particles may be required. In certain instances, particles at sizes of 120 μm and below are preferably used with plasma and serum.

Methods for making such beads are known in the art. For instance, suitable polyethylene beads and other polyolefin beads are produced directly during certain synthesis processes. In some instances, the beads are processed to the required size and shape. Other polymers may need to be ground or spray dried and classified, or otherwise processed to create beads of the desired size distribution and shape.

Beads can be sintered into a monolithic porous structure through either chemical or physical means. Polyethylene beads can be sintered by heating the beads above their melting temperature in a cartridge and applying pressure. The resulting interstitial pore size is slightly reduced from the interstitial pore size of a packed bed of non-sintered beads of equal size. This reduction can be determined empirically and used to produce the desired final interstitial pore size.

The solid substrate may comprise one or more hollow or solid fibers. In an embodiment of the inventive device, wherein the solid substrate comprises hollow fibers, the hollow fibers may preferably comprise a material selected from the group consisting of polysulfones, polyfluorocarbons, polyamides, polynitriles, polypropylenes, cross linked alginates, and cellulose. Other materials commonly used in hollow fibers for medical applications may also be employed. The hollow fiber may preferably comprise a polysulfone.

The size and porosity of the solid substrate should be selected for each application or treatment so as to allow a suitable blood flow rate through the device at an acceptable pressure drop over the device. For certain applications requiring a high blood flow rate and a low pressure drop, a larger diameter particle, pore, hollow fiber or other solid substrate is required. In other applications that do not require a high blood flow rate and a low pressure drop, smaller diameter particles, pores, hollow fibers or other solid substrates may be used. In an embodiment of the present invention, wherein the solid substrate is present in the form of hollow fibers, the inner diameter of the fibers may be in the range of 1 μm to 1000 μm, such as 10, 20, 30, 40, 50, 60, 70, 80, 90, 100, 200, 300, 400, 500, 600, 700, 800, 900 or 1000 μm. Generally, an inner diameter in the range of 20-200 μm is useful, but in certain applications larger or smaller diameter fibers may be employed.

The adsorption media is selected according to the use of the device. For instance, a particular media is used to remove a particular drug of interest. Any drug or poison that binds to the adsorption media can be removed by the device provided herein. The drug can be, for example, an active or inactive ingredient of an analgesic, a sedative, a cosmetics or personal care product, a household cleaning substance, a sedative, a hypnotic, an antipsychotic, an antidepressant, a cardiovascular drug, an antihistamine, a topical preparation, a pesticide, a vitamin, a cold and cough preparation, a stimulant, a street drug, an antibiotic, an antimicrobial, a hormone, a hormone antagonist, an anticonvulsant, a muscle relaxant, a gastrointestinal preparation, a dietary supplement, a diuretic, or an herbal or homeopathic remedy. In some embodiments, the drug is carbamazepine.

In some embodiments, the drug is an antibiotic. The antibiotic can have entered the subject through systemic routes, such as through oral, intravenous, or intramuscular administration. Alternatively, the antibiotic can have entered the subject through topical routes, such as dermal, otic, ophthalmic, or nasal application. Examples of antibiotics include diethylcarbamazine, levamisole, carbamazepine, ceftazidime, daptomycin, fosfomycin, linezolid, vancomycin, amikacin, gentamycin, kanamycin, neomycin, netilmicin, tobramycin, paromycin, streptomycin, spectinomycin, geldanamycin, herbimycin, rifaximin, loracarbef, ertapenem, doripenem, imipenem, cilastatin, meropenem, cefadroxil, cefazolin, cefatolin, cephalexin, cefalcor, cefamandole, cefoxitin, cefprozil, cefuroxime, cefixime, cefdinir, cefditoren, cefoperazone, cefotaxime, cefpodoxime, ceftibuten, ceftizoxime, ceftriaxone, cefepime, ceftaroline fosamil, ceftobiprole, teicoplanin, telavancin, dalbavancin, oritavancin, clindamycin, lincomycin, azithromycin, clarithromycin, dirithromycin, erythromycin, roxithromycin, troleandomycin, telithromycin, spiramycin, aztreonam, furazolidone, nitrofurantoin, posizolid, radezolid, torezolid, amoxicillin, ampicillin, azlocillin, carbenicillim, cloxacillin, dicloxacillin, flucloxacillin, mezlocillin, methicillin, nafcillin, oxacillin, penicillin, piperacillin, temocillin, ticarcillin, bacitracin, colistin, polymyxin, ciproflaxin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, sulfadimethoxine, sulfamethizole, sulfamethoxazole, sulfasalazine, sulfisoxazole, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, arsphenamine, chloramphenicol, fusidic acid, metronidazole, mupirocin, platensimycin, quinupristin, dalfopristin, thiamphenicol, tigecycline, tinidazole, and trimethoprim. In some embodiments, the antibiotic is ceftazidime, daptomycin, fosfomycin, linezolid, or vancomycin. In some embodiments, the antibiotic is vancomycin.

The adsorption media and the drug can form an adhering complex, wherein molecules of the drug are attached to molecules of the adsorption media. The attachment can be, for example, physical or chemical. The attachment can be in the form of one or more chemical bonds such as covalent bonds, ionic bonds, metallic bonds, or hydrogen bonds. Without being bound to any particular theory, the inventors believe that the interaction between the adsorption media and antibiotic drugs is ionic in nature. The adhering complex can comprise individual drug molecules that are each attached to a plurality of molecules of the adsorption media. The adhering complex can comprise individual adsorption media molecules that are each attached to a plurality of molecules of the drug. The adhering complex can comprise individual drug molecules that are each attached to one molecule of the adhering complex.

The contacting of the method forms a cleaned sample that is characterized by a reduced concentration of drug relative to that of the sample prior to contacting the adsorption media. In some embodiments, the concentration of drug is reduced by about 1%, about 2%, about 3%, about 4%, about 5%, about 6%, about 7%, about 8%, about 9%, about 10%, about 12%, about 14%, about 16%, about 18%, about 20%, about 22%, about 24%, about 26%, about 28%, about 30%, about 32%, about 34%, about 36%, about 38%, about 40%, about 45%, about 50%, about 55%, about 60%, about 65%, about 70%, about 75%, about 80%, about 85%, about 90%, about 95%, or about 100%. In some embodiments, the cleansed sample has a drug content that is reduced by about 10% to about 100% from the sample. In certain instances, the sample such as blood flows or passes through the absorbate in an iterative fashion to increase the efficiencies of removal.

The cleansed sample can be formed through a separation of the sample from the adhering complex. As a portion of the drug that was present in the initial sample remains as part of the adhering complex, the resulting separated sample is in a cleansed state with a reduced concentration of drug. The separating can be achieved by, for example, movement of the sample relative to the adhering complex. The movement can be by, for example, diffusion or forced convective flow. In some embodiments, the flow of the sample relative to the adhering complex is driven by a pump, such as a positive displacement pump, an impulse pump, a velocity pump, a gravity pump, or a valveless pump. In some embodiments, the pump is a centrifugal pump. In some embodiments, the flow of the sample relative to the adhering complex is driven by the cardiac activity of the subject.

In therapeutic indications, the cleansed sample is returned by reinfusion into the subject. The cleansed sample can be infused into the subject immediately after it is formed. The cleansed sample can be held for any period of time prior to infusion into the subject. One or more components can be added to the cleansed sample subsequent to its formation and prior to the infusion. In some embodiments, liquid is added to the cleansed sample to adjust its volume subsequent to its formation and prior to the infusion. The infusion can be in the form of a discrete volume of sample cleansed with the method. The infusion can be in the form a continuous or semi-continuous stream. The amount of cleansed sample that can be infused in the claimed methods is not intended to be limited. It can range from less than 1 mL to above 1 L, up to and including the entire blood volume of the patient when the sample comprises blood and when continuous recirculation back to the subject is employed. One or more 'passes' through the adsorption bed may be used if needed. In some embodiments, the cleansed sample is infused into the subject at a rate of about 5 mL/min, about 10 mL/min, about 15 mL/min, about 20 mL/min, about 25 mL/min, about 30 mL/min, about 35 mL/min, about 40 mL/min, about 45 mL/min, about 50 mL/min, about 60 mL/min, about 70 mL/min, about 80 mL/min, about 90 mL/min, about 100 mL/min, about 150 mL/min, about 200 mL/min, about 250 mL/min, about 300 mL/min, about 350 mL/min, about 400 mL/min, about 450 mL/min, about 500 mL/min, about 550 mL/min, about 600 mL/min, about 700 mL/min, about 800 mL/min, about 900 mL/min, or about 1000 mL/min.

Other uses for the methods include non-therapeutic indications in diagnostics, blood banking and the treatment/purification of process streams, e.g., in biotechnology manufacturing. Clinical and hospital laboratories can find useful applications of the technology. In fact, a skilled person will appreciate in one aspect, the invention provides a method of first determining in vitro whether a particular drug binds to the column as well as the drug's binding efficiency. Thereafter, the methods herein can be used to treat patients. In this manner, the methods provide identifying drugs and poisons that the methods are useful in removing. A skilled artisan will appreciate that various impurities and poisons can be removed from human, biological, chemical and manufacturing samples using the methods described herein.

Also provided are devices for treating drug intoxication in a subject in need thereof. The devices are characterized by a cartridge containing the adsorption media, influx and efflux ports to allow the sample to flow into and out of the device, and endplates to prevent substantially all of the adsorption media from exiting the cartridge. One such device is disclosed in U.S. patent application Ser. No. 14/860,589, filed Sep. 21, 2015.

Figure 2:
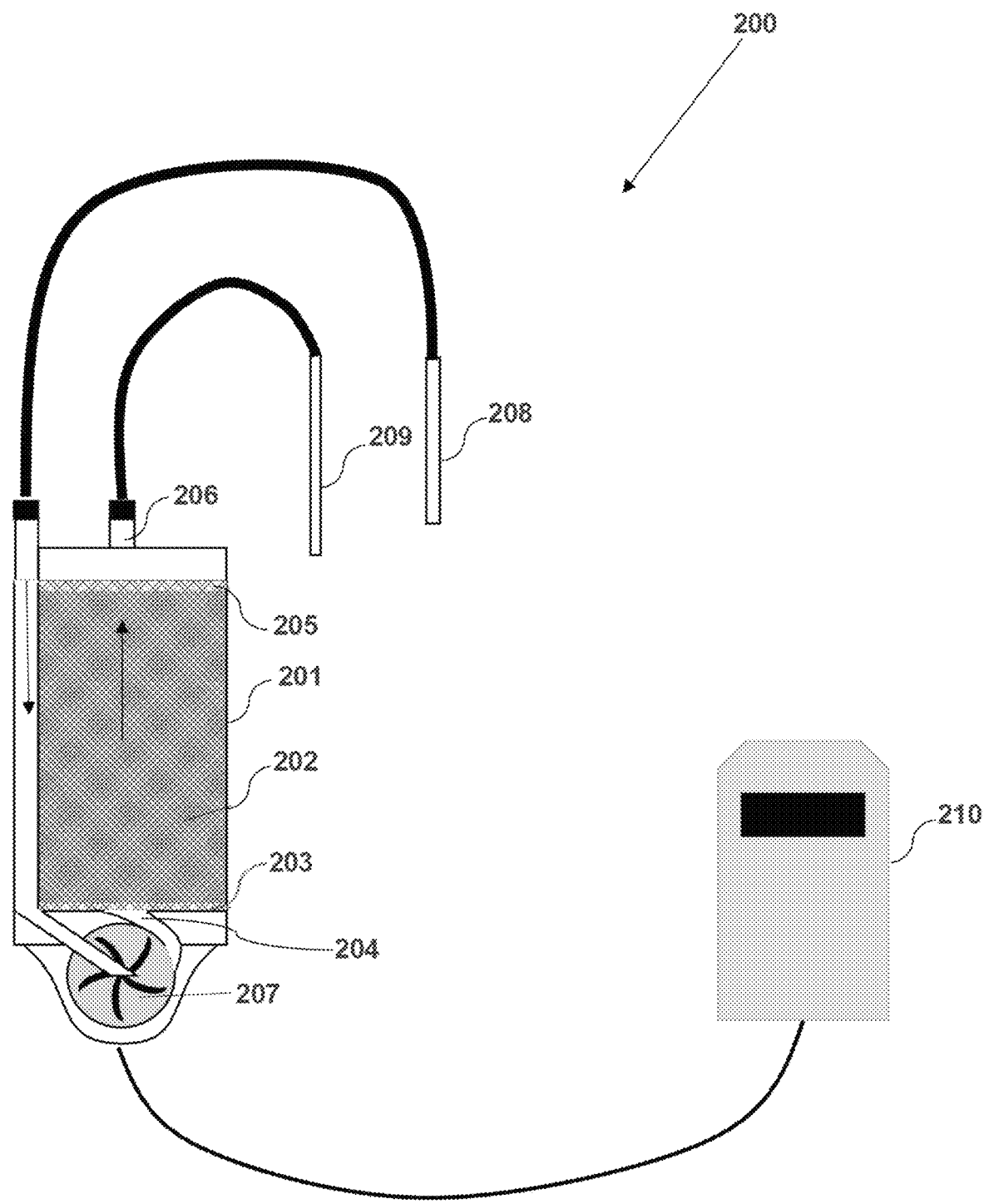
FIG. 2 is an illustration of a device in accordance with an embodiment.
Figure 3A:
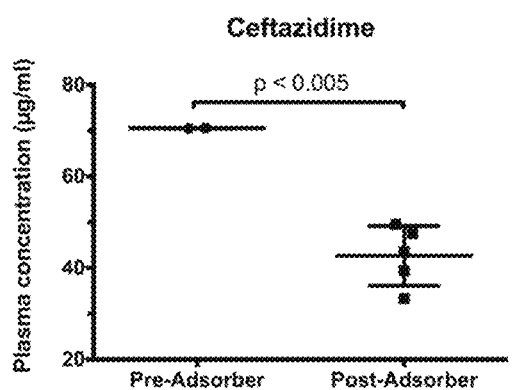
FIG. 3A-D is a series of four graphs (A-D) showing results obtained with an embodiment.
Figure 3B:
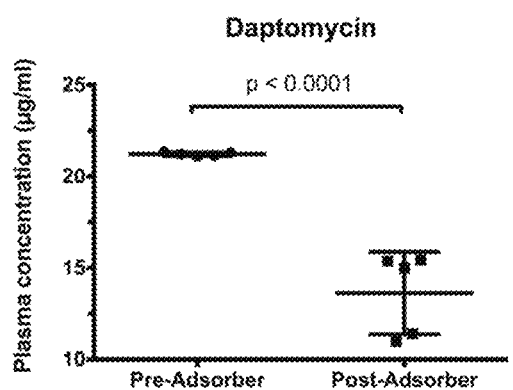
Figure 3C:
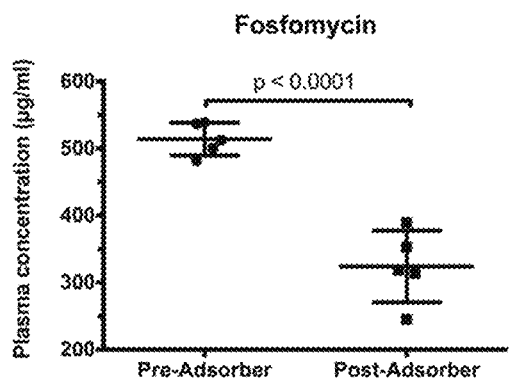
Figure 3D:
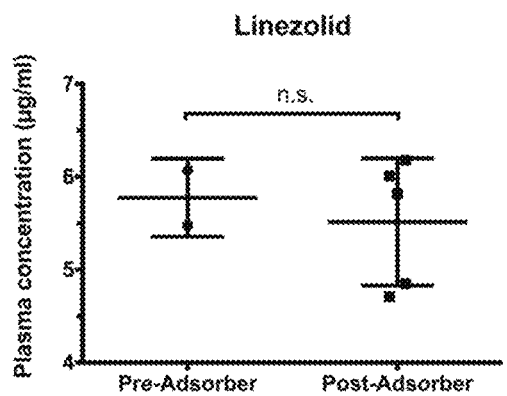

FIG. 2 illustrates one embodiment. Shown in device 200 is a cartridge 201 that holds adsorption media 202. The cartridge further has a first porous endplate 203 that is proximate to an inlet port 204, and a second porous endplate 205 that is proximate to an efflux port 206. A centrifugal pump 207 forces convective flow of the sample through the cartridge 201 in through the inlet port 204 and first endplate 203, in contact with the adsorption media 202, and out through the second endplate 205 and efflux port 206. The centrifugal pump 207 is in fluid connection with an arterial catheter 208 and a venous catheter 209. Typically, a sample is withdrawn from the subject and input into the device through the arterial catheter 208. The cleansed sample is output from the device and infused into the subject through the venous catheter 209. The centrifugal pump 207 is also in electrical connection with a controller 210 that controls the activity of the pump and optionally provides electrical power to the pump.

The device can be intracorporeal or extracorporeal. If used extracorporeally, it can comprise a conventional device for extracorporeal treatment of blood and serum from patients. For example, a cartridge or column can then be used in series with conventional extracorporeal circuits such as those of cardiopulmonary bypass, hemodialysis, and oxygenation. The device can also be used as a shunt or alternative to other filters, so that before or after oxygenation the blood flow to the oxygenation mechanism is shunted to the present media for removal of endotoxins. The present media can also be used as the sole element in an extracorporeal blood flow circuit.

In some embodiments, the cartridge has a cylindrical shape. In other embodiments, the cartridge has a contoured shape that facilitates wearing the device on a leg or arm. In yet other aspects, the cartridge has a brick or rectangular block shape which can optimize storage volume.

In some embodiments, and as is shown in FIG. 2, the device comprises a pump in series with the adsorption media to drive increased flow of the sample across and/or through the adsorption media. The pump may optionally be integrated into the extracorporeal cartridge to reduce size and weight. Pumps such as centrifugal pumps that are integrated into the cartridge include, but are not limited to, Flow Forward Medical's The Arteriovenous Fistula Eligibility (AFE) System™ or the HeartWare®'s Circulite® Synergy Pocket Circulatory Assist Device (CAD). Alternatively, sample flow can be driven by another type of positive displacement pump, an impulse pump, a velocity pump, a gravity pump, or a valveless pump. In some embodiments, sample flow is driven by the cardiac activity of the subject. Flow through the cartridge can be controlled to optimize the interaction of the drug with the adsorption media. Inlet flow can be controlled using established methods in order to prevent vein collapse.

In some embodiments, and as is shown in FIG. 2, the device comprises a single lumen arterial catheter to withdraw the sample from the subject and a single lumen venous catheter to infuse the cleansed sample into the subject. In some embodiments, the device comprises a dual lumen catheter or needle to handle both the supply and the return of the sample. In some embodiments, single lumen catheters are used for venous supply and venous return.

In some embodiments, and as is shown in FIG. 2, the device comprises a controller and/or a power source. A power source and computer control can be optionally built into the pump module of the device. In other aspects, a separate, wearable power supply is used, and optionally, reused if connected to a subsequent device. For disposal purposes, a battery or power source and computer module can be ejected from the integrated device prior to disposal or incineration.

The devices and methods can utilize a computing apparatus that is programmed or otherwise configured to automate and/or regulate one or more steps of the methods or features of the devices provided herein. Some embodiments provide machine executable code in a non-transitory storage medium that, when executed by a computing apparatus, implements any of the methods or operates any of the devices described herein. In some embodiments, the computing apparatus operates the power source and/or pump control.

The holdup volume of the device can be minimized, and a volume of sterile saline can be included into the integrated device for circuit priming and de-airing. Additional safety features include, but are not limited to, a venous return line bubble trap, pressure sensors, and screen filters. Systemic anticoagulation control can also be added and controlled through Venturi liquid injection.

The methods and device herein take advantage of the adsorption capacity of actived carbon. It is applicable to many cases of severe drug intoxication. During this procedure the patient's blood is continuously perfused through a small cartridge containing a combination of charcoal granules and heparin.

EXAMPLES

The following examples are offered to illustrate the embodiments described in detail above, and are not intended to be limiting in any way.

Example 1

Five different antibiotics were tested individually using miniature 1-mL minicartridges that were filled with heparinized media. The five antibiotics included daptomycin, fosfomycin, linezolid, vancomycin and ceftazidime. Each minicartridge was first primed with 2 mL of saline. For each antibiotic a quantity of blood was spiked to a desired therapeutic concentration of antibiotic and mixed for 5 minutes. To determine the initial 'pre-filtered' plasma concentration, a small sample was centrifuged for 10 minutes and tested. Subsequently, 2 mL of blood with the antibiotic was passed through the primed minicartridge over 20 second. The 'filtered' blood was then collected. The plasma concentration of each antibiotic was then determined after centrifugation of the blood for 10 minutes.

FIG. 3 presents data from each of the five tests, showing the concentration of drug in the plasma both before and after contacting the samples with the adsorption media. FIG. 3A shows the reduction in concentration for ceftazidime. FIG. 3B shows the reduction in concentration for daptomycin. FIG. 3C shows the reduction in concentration for fosfomycin. FIG. 3D shows the reduction in concentration for vancomycin.

Example 2

Example 2 illustrates treating drug intoxication in a subject without hardware or instrumentation.

Arterial to venous flow (with optional vasopressors) using blood pressure difference to generate flow through absorbate. Drug intoxication treatment via a single-needle venous line by using a standard blood bag with adsorbent 'filter' inserted into the blood tubing. (Vasopressors may be required with hypotension, although slow flow during collection is compensated by and more rapid reinfusion.)

Once the blood bag fills (≥10 min) it is raised above the patient, flowing back through the standard blood bag with adsorbent 'filter' for a second treatment. Since direction of flow does not affect performance, the single unit of blood gets two passes before returning to the patient, affecting a major reduction in the drug or toxin. The process can be repeated several times as needed. Using a low-cost blood bag and needle set eliminates the need for any hardware or instrumentation (an IV pole or even two nails could suffice) and greatly reduces the need for monitoring by healthcare workers.

Figure 4A:
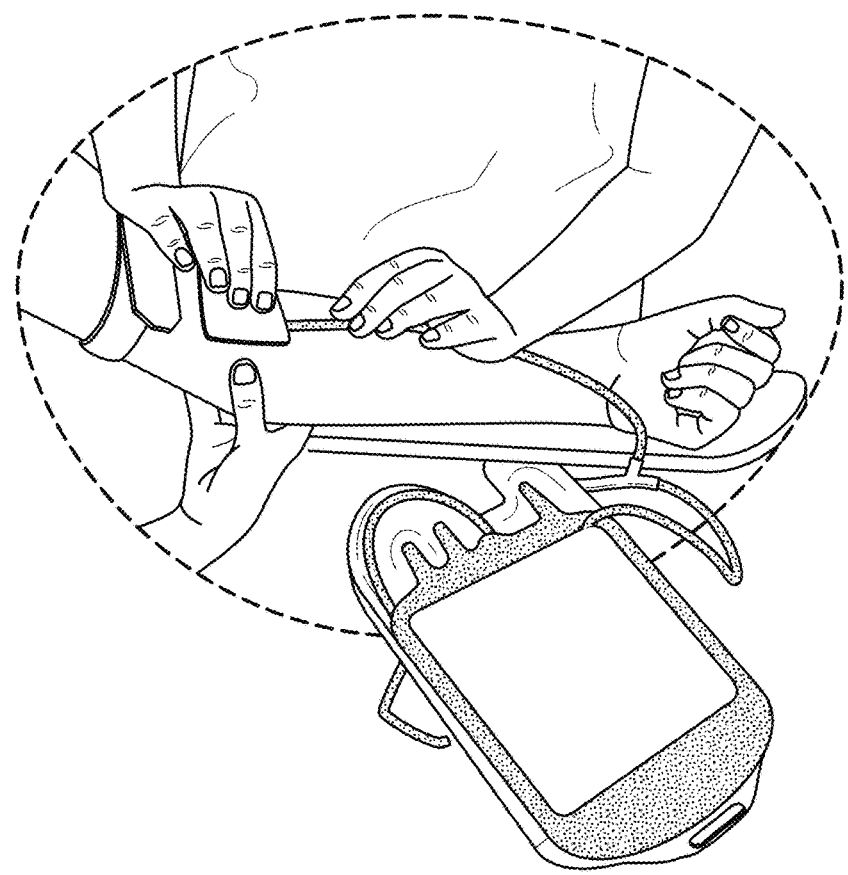
FIGS. 4A-B illustrate drug intoxication treatment without hardware or instrumentation.
Figure 4B:
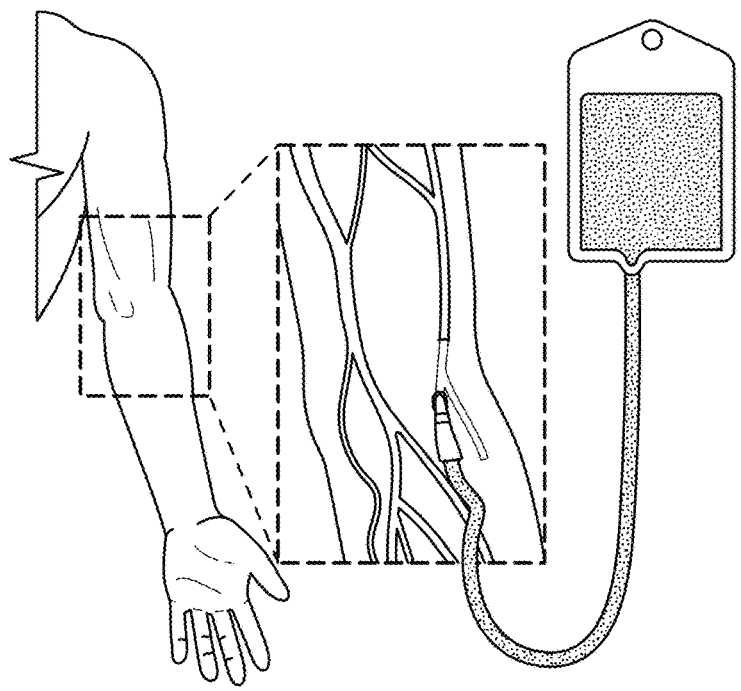

FIG. 4A illustrates contacting a blood sample from a subject suffering from drug intoxication with an adsorption media to form a cleansed sample. FIG. 4B shows autologous transfusion of purified blood through a filter and infusing the cleansed sample into the subject.

Example 3

Example 3 illustrates a side-by-side blood compatibility test performed on a FDA approved charcoal filter and a test device.

Figure 5:
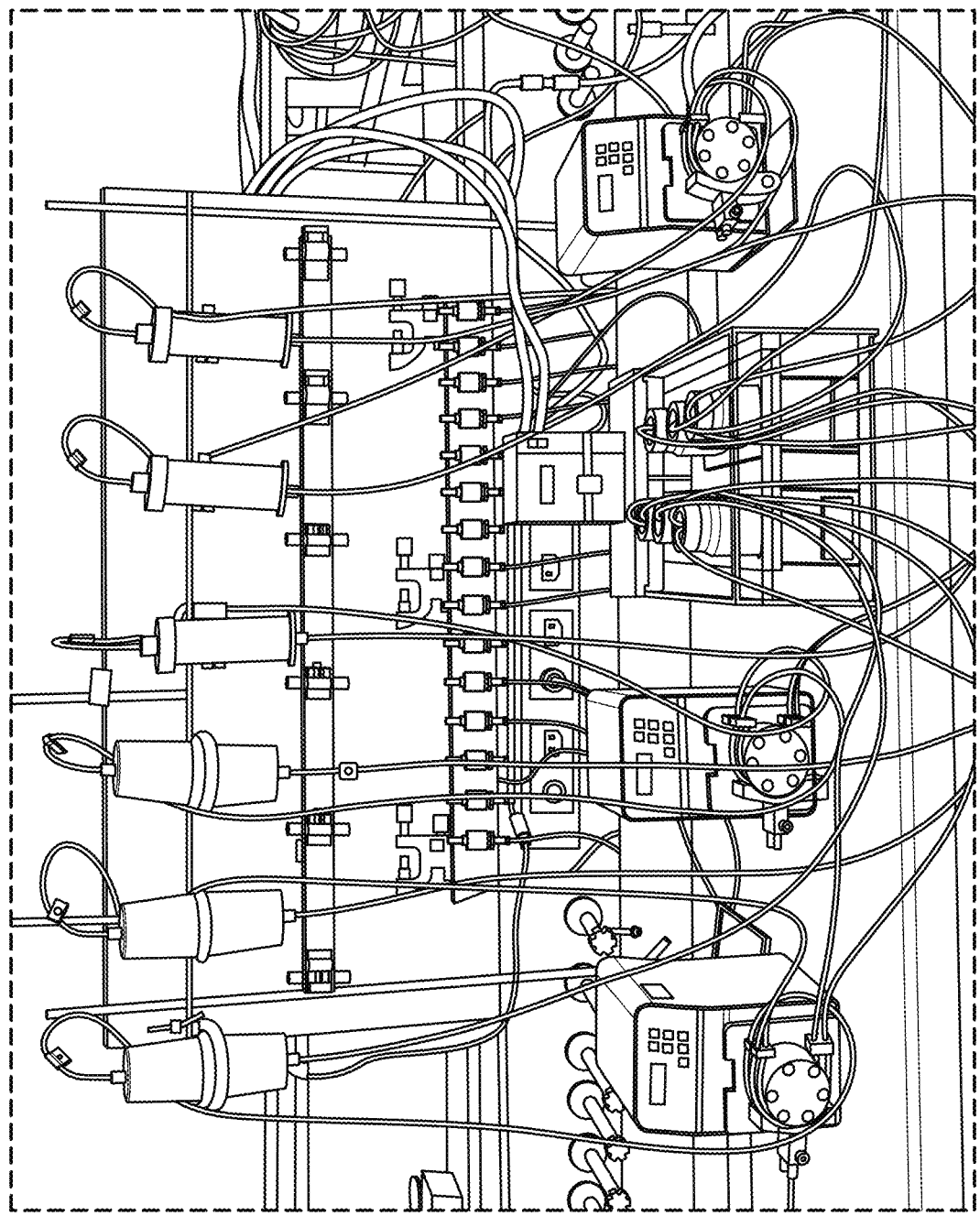
FIG. 5 illustrates a side-by-side comparison of two blood filter devices.

This example compares performance on filtering blood by two devices, a FDA approved charcoal filter, Gambro Adsorba® Hemoperfusion Cartridge 300 C ("Gambro"), and, Exthera Medical Seraph® 100 Microbind® Affinity Blood Filter ("Seraph"). Seraph is a first-of-its-kind blood filter designed to reduce pathogens from the bloodstream during infections in adjunction to antibiotic treatment. Harmful substances are captured and adsorbed onto the device's proprietary surface. The example performed ex vivo experiments with heparinized human blood to study hemolysis, thrombocytopenia and hypocalcemia of the Seraph device as compared to a predicated hemoperfusion device, Gambro (FIG. 5). In FIG. 5, the 3 devices on the right are the Seraph® devices. The three devices on the left, are the Gambro Adsorba® Hemoperfusion Cartridge 300 C devices.

Materials as used are listed in Table 1 below.

TABLE 1

| Device | Sterilization mode | Priming volume [mL] | Lot | Exp. Date | Remark |
|---|---|---|---|---|---|
| ExThera Medical Seraph ® 100 Microbind ® Affinity Blood Filter ExThera Medical (Test device) | EO | 160 | 7-461 | 2022-11 | — |
| Gambro Adsorba ® Hemoperfusion Cartridge 300 C Gambro Dialysatoren GmbH (Predicate device) | Steam | 260 | K004919 | 2020-06 | Prefilled with saline 0.9% |

Methods

For the testing, freshly donated human blood (drawn at the Medical Service, ICO Obernburg, Germany) was used within 1 h after blood drawing. For anticoagulation, blood was prepared to 3.5 IU/mL with unfractionated heparin (#H3149, Sigma Aldrich, Steinheim, Germany).

Blood from two single donors (500 mL each, ABO compatible) was pooled and therefore, the test adsorber and the predicate device was tested in a paired fashion using identical circuits with the same pool of blood: Two circuits with blood pump (Ismatec MPC, Mondfeld Germany) and tubing set (AV 1000, Promedt Medizintechnik GmbH, Germany) were assembled, one containing the test device (Seraph® 100 Microbind® Affinity Blood Filter) and the other containing the comparator device (Gambro Adsorba® Hemoperfusion Cartridge 300 C).

Each device was primed by recirculating 1 L of saline at 250 mL/min for 30 min, followed by flushing 1 L saline at 60 mL/min in single pass. Saline in the blood circuit was replaced by human blood without generating an air/blood interface. 500 mL blood was recirculated with a blood flow rate of 350 mL/min (maximum labeled blood flow rate) for up to 8 h at 37° C. After 3 min of recirculation at 37°±1° C., two 3 mL samples were taken from the arterial port of the blood tubing sets. Further samples (3 mL each) were taken at time points 0.5, 1, 2, 3, 4, 5, 6, 7 and 8 hours for the measurement of plasma free hemoglobin (hemolysis), total hemoglobin tHb, hematocrit (Hct), red blood cell (RBC) count, and $Ca^{2+}$. Thus, at each time point there were duplicate measurements of the parameters tHb, fHb, Hct, RBC, and $Ca^{2+}$.

In parallel, static blood controls were collected from a small volume of the same blood pool used for the test of the devices before start (t0=0 h) and after storage in an incubator for 8 h at 37° C. for the measurement of free hemoglobin (hemolysis), total hemoglobin tHb, hematocrit (Hct), red blood cell (RBC) count, and $Ca^{2+}$. This setup was repeated five times, leading to five independent measurements with five different blood pools for every adsorber type (n=5 replicates each).

Total Hb was measured on the ABX Pentra 60 (Reichenbach, Germany). Free Hb was determined by photometry at three wavelengths to correct for background (A380 nm, A415 nm, A450 nm, photometer UV1650PC, Shimadzu Deutschland GmbH). The following equation was used to calculate plasma free hemoglobin [fHb]:

$$fHb_{plasma} = ((168 * A_{415\,nm}) - (^{84}*A380\,nm) - (84*A_{450\,nm})) * (VF_{11})\ [g/dl]$$

VF: dilution factor

Hemolysis was reported in two ways over time: (a) as free hemoglobin [fHb]; and (b) as % hemolysis relative to total hemoglobin [tHb] in mg/L obtained after red cell lysis at t=0 min.

Blood parameters such as hematocrit, red blood cell count (RBC) were measured on the ABX Pentra 60 (Reichenbach, Germany). $Ca^{2+}$ was measured using a Cobas c111 clinical analyzer (Roche Diagnostics GmbH, Mannheim, Germany).

Arterial and venous pressure (bloodin, bloodout) was recorded with the multichannel pressure transducer (DPT-6300, Codan pvb Medical GmbH, Forstinning, Germany) and a laboratory data acquisition system (MSR-manager, HITEC Zang, Herzogenrath, Germany).

Data analysis of the respective parameters was performed for time points 4 h and 8 h by two way ANOVA following pairwise comparison after Tukey using the software Minitab release 17 (Additive GmbH, Friedrichsdorf, Germany). A statistical model was built in which the factors blood pool and device type will be taken into account. A probability of P<0.05 will be considered as significant.

Results and Discussion

The results over time are summarized in Tables 2-4 (mean±SD from n=5 experiments) below and in FIGS. 6A-F.

TABLE 2 fHb [mg/dL] and hemolysis [%] in human plasma at different time points

| | fHb [mg/dL] | | Hemolysis [%] | |
|---|---|---|---|---|
| Time | ExThera Medical Seraph ® 100 | Gambro Adsorba ® 300 C | ExThera Medical Seraph ® 100 | Gambro Adsorba ® 300 C |
| 0 min | 4 ± 4 | 4 ± 4 | 0.03 ± 0.03 | 0.03 ± 0.03 |
| 3 min | 3 ± 1 | 3 ± 1 | 0.02 ± 0.01 | 0.02 ± 0.01 |
| 0.5 h | 7 ± 0 | 10 ± 2 | 0.04 ± 0.00 | 0.07 ± 0.01 |
| 1 h | 12 ± 1 | 20 ± 4 | 0.08 ± 0.01 | 0.13 ± 0.03 |
| 2 h | 22 ± 4 | 35 ± 8 | 0.14 ± 0.03 | 0.24 ± 0.05 |

TABLE 2-continued fHb [mg/dL] and hemolysis [%] in human plasma at different time points

| | fHb [mg/dL] | | Hemolysis [%] | |
|---|---|---|---|---|
| Time | ExThera Medical Seraph ® 100 | Gambro Adsorba ® 300 C | ExThera Medical Seraph ® 100 | Gambro Adsorba ® 300 C |
| 3 h | 34 ± 6 | 53 ± 12 | 0.22 ± 0.03 | 0.36 ± 0.08 |
| 4 h | 46* ± 9 | 71 ± 18 | 0.31* ± 0.05 | 0.48 ± 0.11 |
| 5 h | 58 ± 11 | 84 ± 18 | 0.38 ± 0.06 | 0.57 ± 0.11 |
| 6 h | 72 ± 13 | 108 ± 27 | 0.48 ± 0.07 | 0.73 ± 0.17 |
| 7 h | 90 ± 18 | 124 ± 28 | 0.59 ± 0.09 | 0.84 ± 0.16 |
| 8 h | 107* ± 25 | 142 ± 31 | 0.71* ± 0.13 | 0.95 ± 0.18 |
| Control 8 h | 4 ± 1 | 4 ± 1 | 0.03 ± 0.01 | 0.03 ± 0.01 |

*means are statistically significantly different from each other (P < 0.05). Compare only data pairs with the same parameter and at t = 4 h and 8 h.

TABLE 3

RBC [%] and Hct [%] in human blood at different time points

| | RBC [%] | | Hct [%] | |
|---|---|---|---|---|
| Time | ExThera Medical Seraph ® 100 | Gambro Adsorba ® 300 C | ExThera Medical Seraph ® 100 | Gambro Adsorba ® 300 C |
| 0 min | 100 ± 0 | 100 ± 0 | 45.8 ± 2.1 | 45.8 ± 2.1 |
| 3 min | 99 ± 1 | 98 ± 1 | 45.5 ± 2.3 | 44.6 ± 2.2 |
| 0.5 h | 99 ± 1 | 97 ± 1 | 45.3 ± 2.5 | 44.6 ± 2.4 |
| 1 h | 99 ± 1 | 97 ± 1 | 45.2 ± 2.3 | 44.4 ± 2.1 |
| 2 h | 98 ± 1 | 97 ± 1 | 45.0 ± 2.3 | 44.4 ± 2.2 |
| 3 h | 99 ± 1 | 97 ± 1 | 45.1 ± 2.3 | 44.4 ± 2.4 |
| 4 h | 98* ± 1 | 97 ± 1 | 45.0* ± 2.0 | 44.5 ± 2.4 |
| 5 h | 99 ± 1 | 97 ± 1 | 45.1 ± 2.2 | 44.1 ± 2.2 |
| 6 h | 99 ± 1 | 97 ± 1 | 45.2 ± 2.2 | 44.3 ± 2.3 |
| 7 h | 99 ± 1 | 97 ± 1 | 45.3 ± 2.1 | 44.1 ± 2.3 |
| 8 h | 99* ± 1 | 97 ± 1 | 45.3* ± 2.4 | 44.2 ± 2.3 |
| Control 8 h | 101 ± 2 | 101 ± 2 | 46.7 ± 2.4 | 46.7 ± 2.4 |

*means are statistically significantly different from each other (P < 0.05). Compare only data pairs with the same parameter and at t = 4 h and 8 h.

TABLE 4

$Ca^{2+}$ [mmol/L] in human plasma at different time points

| | $Ca^{2+}$ [mmol/L] | |
|---|---|---|
| Time | ExThera Medical Seraph ® 100 | Gambro Adsorba ® 300 C |
| 0 min | 2.33 ± 0.04 | 2.33 ± 0.04 |
| 3 min | 1.92 ± 0.02 | 0.40 ± 0.03 |
| 0.5 h | 1.80 ± 0.03 | 0.16 ± 0.01 |
| 1 h | 1.79 ± 0.06 | 0.13 ± 0.01 |
| 2 h | 1.80 ± 0.09 | 0.13 ± 0.01 |
| 3 h | 1.81 ± 0.10 | 0.10 ± 0.03 |
| 4 h | 1.77* ± 0.05 | 0.09 ± 0.01 |
| 5 h | 1.80 ± 0.04 | 0.07 ± 0.02 |
| 6 h | 1.79 ± 0.06 | 0.09 ± 0.02 |
| 7 h | 1.78 ± 0.05 | 0.08 ± 0.01 |
| 8 h | 1.80* ± 0.04 | 0.07 ± 0.01 |
| Control 8 h | 2.39 ± 0.05 | 2.39 ± 0.05 |

*means are statistically significantly different from each other (P < 0.05). Compare only data pairs with the same parameter and at t = 4 h and 8 h.

Plasma free hemoglobin (fHb) and hemolysis (%): Damage of red cells and cell lysis results in free plasma hemoglobin. Hemolysis increased linearly till time point 8 h for both adsorber types, in which the Gambro device showed higher hemolysis [%] and fHb [mg/dL] values over time as compared to the test device (Table 2, FIGS. 6A-B). For example, the Gambro device has about 32.7% higher fHb than the test device (Seraph) at time 8 h. The almost linear increase can be likely explained by the repeated passage of the blood through the system (mainly the adsorber and the blood pump). No limit for hemolysis is given by standards or guidelines for medical devices, respectively. However, a limit of 0.8% (Europe) and 1% (USA) is generally accepted for red cell concentrates after storage for 42 days, which can also be seen as a useful reference for hemolysis induced by medical devices.

The ExThera Medical Seraph 100 filter passed both requirements (0.8 and 1.0%) over time. At t=8 h, the predicate device (Gambro) showed hemolysis values >0.8%, but the mean hemolysis value was still below 1%.

Figure 6A:
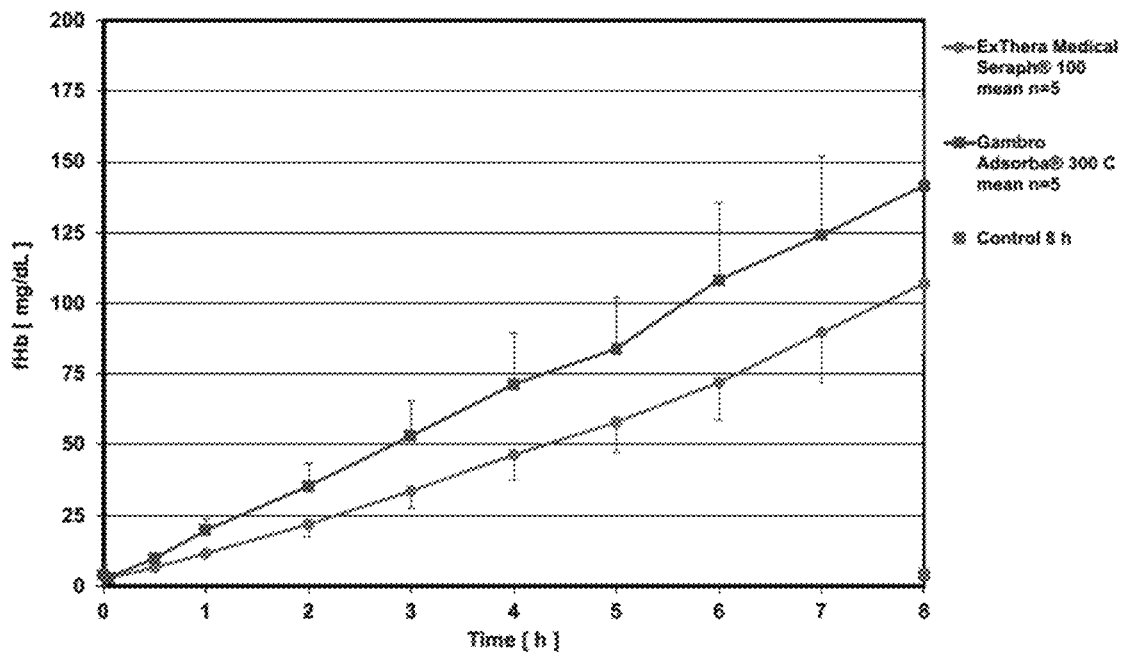
FIGS. 6A-F illustrate measurements of a variety of blood components after filtration.
Figure 6B:
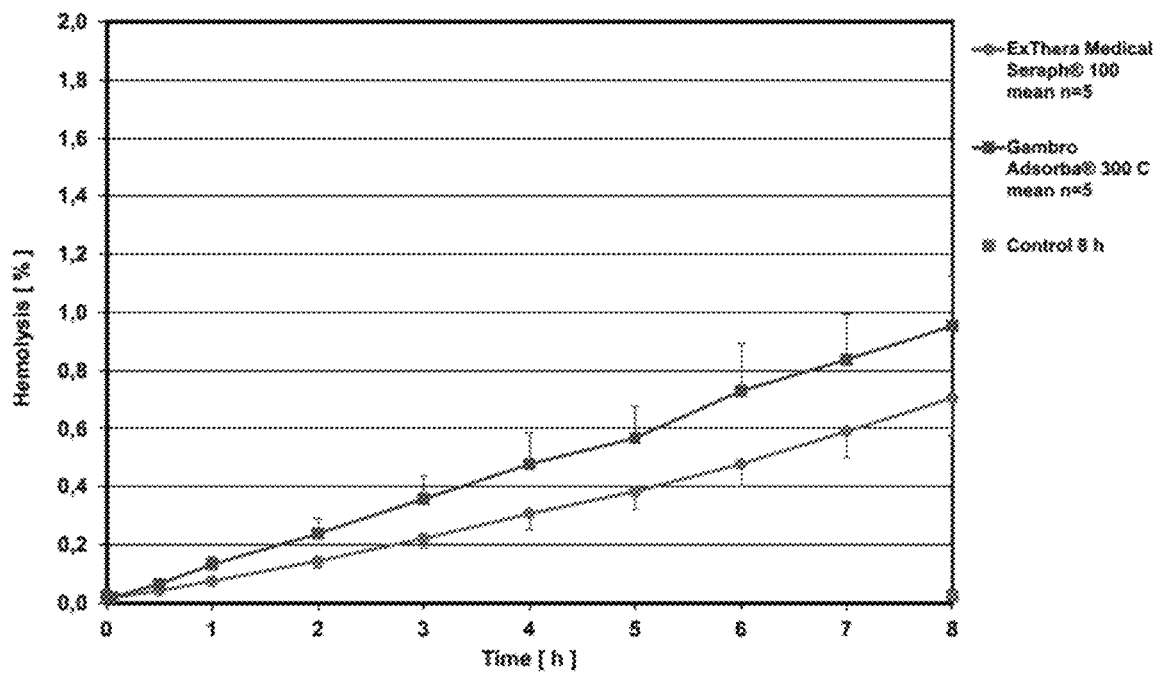
Figure 6C:
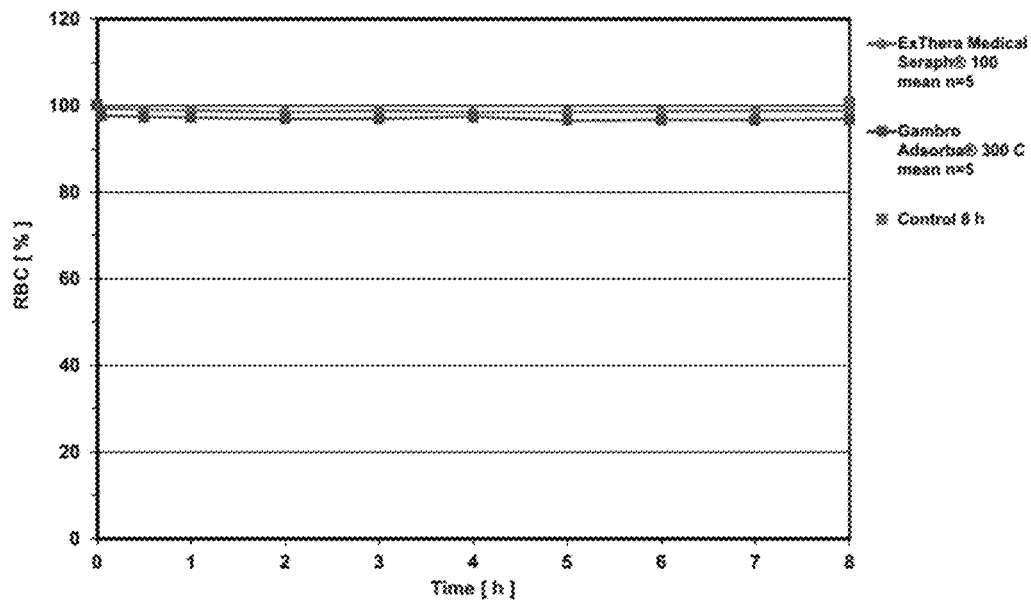
Figure 6D:
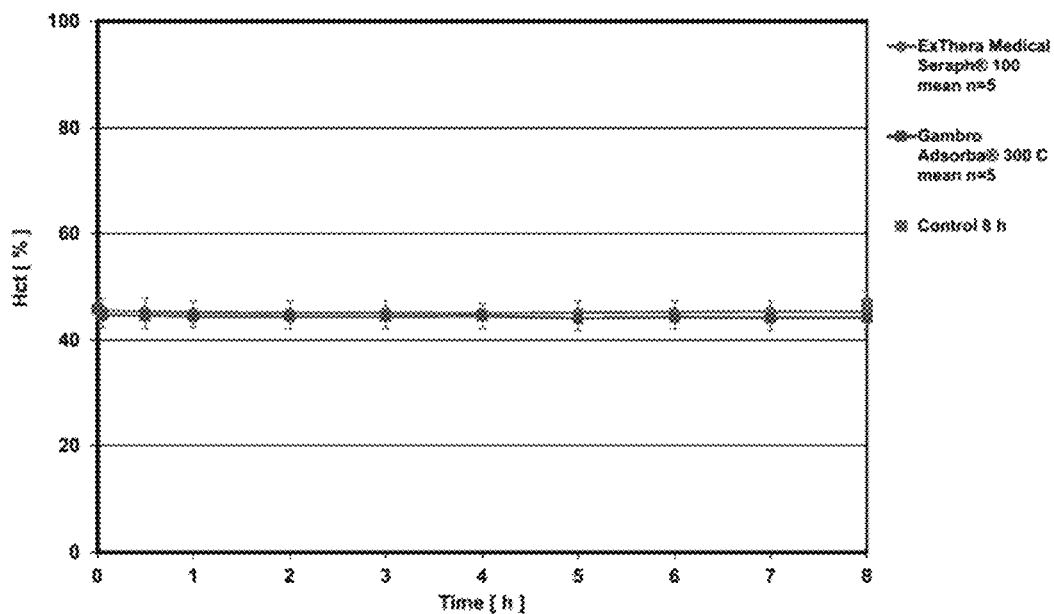

Red blood cell count (RBC) and hematocrit (Hct): A drop in RBC and hematocrit reflects adhesion of the cells within the experimental set up. The drop in red blood cell count is expressed as % of the initial value (Table 3; FIGS. 6C-D). Only a very small drop in RBC and hematocrit was detected for both devices, the ExThera Medical Seraph® 100 filter and the predicate device (Gambro).

First, the adsorber particles are different. In contrast to the test device, which contains polyethylene (PE) beads with covalently bound heparin, the Gambro adsorber is filled with cellulose-coated activated carbon.

Figure 6E:
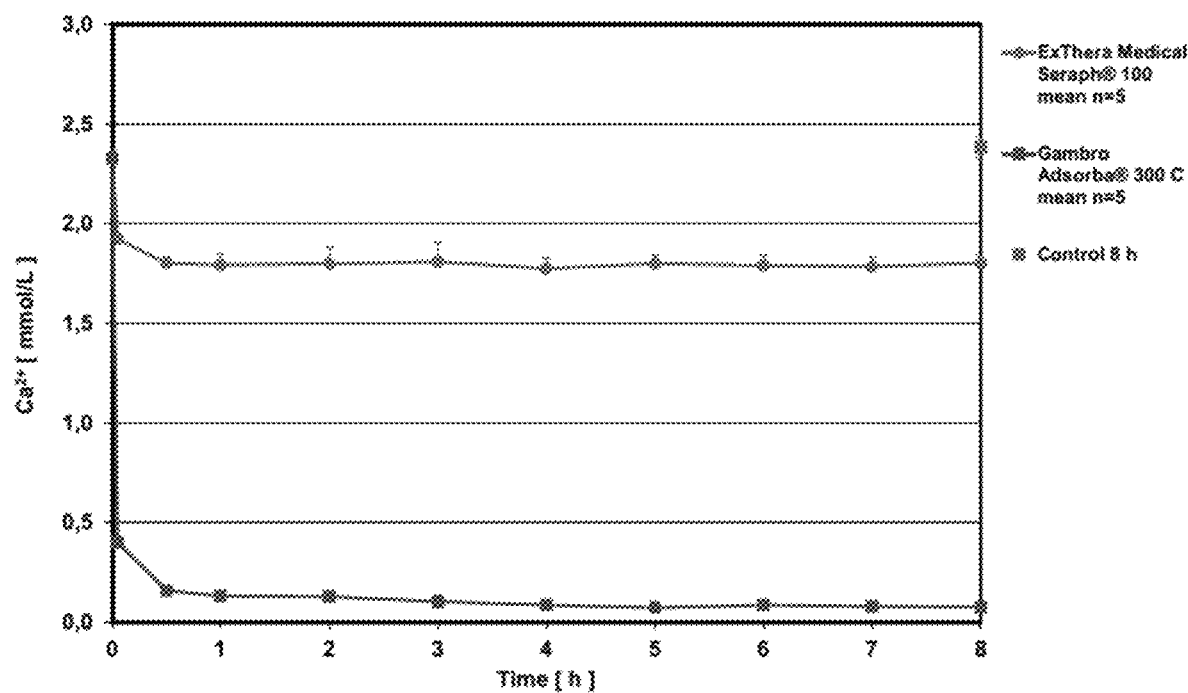

$Ca^{2+}$: $Ca^{2+}$ was almost completely adsorbed by the predicate device already after 30 min (Table 4; FIG. 6E). In contrast, the test device showed constant $Ca^{2+}$ concentrations over time with only a slight decrease after 3 min, probably due to minor dilution of the blood with saline after start.

Figure 6F:
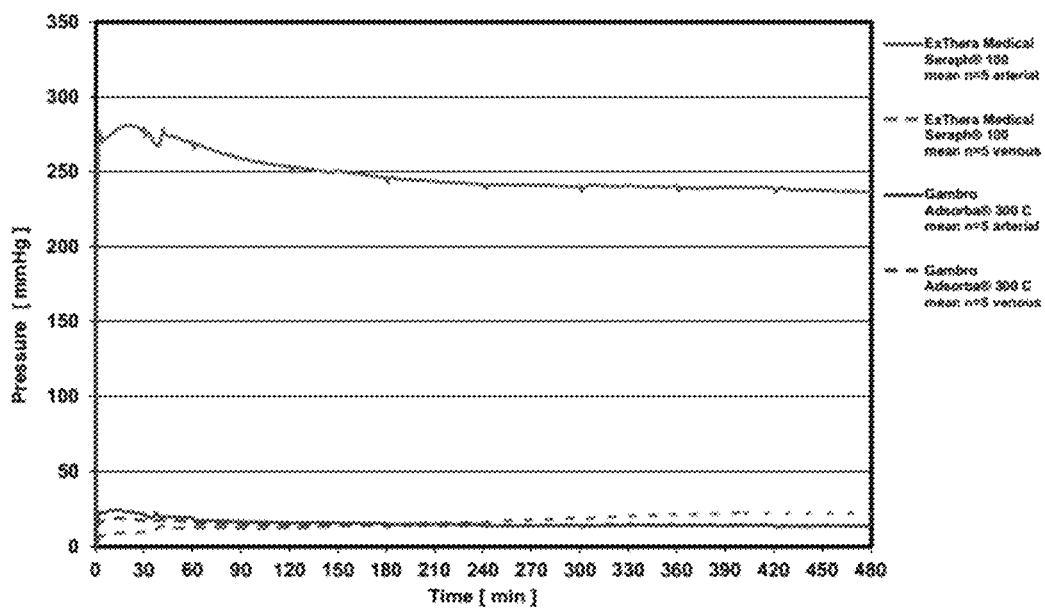

Pressure: The mean arterial pressure of the Seraph® 100 filter was relatively high, between 230 and 280 mmHg and decreased slightly over time (FIG. 6F). The arterial pressure of the predicate device was low, below 25 mmHg and decreased also slightly over time. The difference in arterial pressure between the two devices can be explained by a smaller particle size, and thus, higher packing density of the ExThera adsorber. The venous pressures of both device types were low (<25 mmHg).

CONCLUSION

Statistical differences were observed for all parameters at time point 4 h and 8 h. Nevertheless, the Seraph® 100 Microbind® Affinity Blood Filter and the Gambro Adsorba® 300 C behaved very similar with respect to hematocrit. In general, the results from Seraph were far superior as the blood coming out of the charcoal filter (Gambro) was very dark, whereas the blood coming out of Seraph was bright red or lighter and healthy looking (FIG. 5, Seraph on the right). In contrast, hemolysis and adsorption of $Ca^{2+}$ was larger for the predicate device. $Ca^{2+}$ was almost completely adsorbed by the predicate device already after 30 min (FIG. 6E).

Example 4

Example 4 illustrates filtering blood with a combination of heparin and charcoal/activated carbon filter.

A proof of concept study for blood compatibility on a adsorption media combination of charcoal (activated carbon) and heparin filter will be performed. Blood samples will be collected and processed as described in Example 3. Test samples and controls will be treated in absorbent media comprising charcoal and/or active carbon and heparin and/or heparan sulfate, and measurements of free hemoglobin (hemolysis), total hemoglobin tHb, hematocrit (Hct), red blood cell (RBC) count, platelet count (PC) and $Ca^{2+}$. The set up will be repeated five times, leading to five independent measurements with five different blood pools (n=5 replicates).

The results of hemolysis and adsorption of $Ca^{2+}$ of the adsorption media comprising a combination of charcoal (activated carbon) and heparin filter will be similar to the Seraph® device.

Example 5

Example 5 illustrates treating drug intoxication in blood sample with a combination of activated carbon and heparin.

Five different antibiotics will be tested individually using miniature 1-mL minicartridges or a similar device that is filled with charcoal and/or active carbon and heparin and/or heparan sulfate. The five antibiotics will include daptomycin, fosfomycin, linezolid, vancomycin and ceftazidime. Each minicartridge is first primed with 2 mL of saline. For each antibiotic, a quantity of blood is spiked to a desired therapeutic concentration of antibiotic and mixed for 5 minutes. To determine the initial 'pre-filtered' plasma concentration, a small sample is centrifuged for 10 minutes and tested. Subsequently, 2 mL of blood with the antibiotic is passed through the primed minicartridge over 20 second. The 'filtered' blood is then collected. The plasma concentration of each antibiotic is then determined after centrifugation of the blood for 10 minutes.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, websites, and databases cited herein are hereby incorporated by reference in their entireties for all purposes.

What is claimed is:

1. A method for treating drug intoxication or removing a toxin in a subject in need thereof, said method comprising: contacting a whole blood sample containing a calcium ion ($Ca^{++}$) concentration from a subject suffering from drug intoxication or other intoxication with an adsorption media comprising a combination of activated carbon and a substrate having at least one polysaccharide adsorbent to form a cleansed sample, wherein the at least one polysaccharide adsorbent is a member selected from the group consisting of heparin and heparan sulfate; and infusing the cleansed sample into the subject, wherein the cleansed sample comprise a near constant calcium ion ($Ca^{++}$) concentration.

2. The method of claim 1, wherein the adsorption media and the drug form an adhering complex.

3. The method of claim 2, further comprising separating the whole blood sample from the adhering complex to produce the cleansed sample with a reduced amount of drug.

4. The method of claim 1, wherein the drug is a member selected from the group consisting of analgesics, sedatives, hypnotics, antipsychotics, antidepressants cardiovascular drugs, antihistamines, topical preparations, cold and cough preparations, stimulants, street drugs, recreational drugs, antibiotics, antimicrobials, hormones, hormone antagonists, anticonvulsants, gastrointestinal preparations, dietary supplements, and herbals.

5. The method of claim 4, wherein the drug is an antibiotic.

6. The method of claim 1, wherein the adsorption media comprises a solid substrate having at least one polysaccharide adsorbent.

7. The method of claim 6, wherein the least one polysaccharide adsorbent further comprises hyaluronic acid, sialic acid, carbohydrates with mannose sequences, chitosan, or a combination thereof.

8. The method of claim 1, wherein the least one polysaccharide adsorbent is heparin.

9. The method of claim 1, wherein the adsorption media comprises about 10 wt. % to about 90 wt. % of heparin and/or heparan sulfate.

10. The method of claim 6, wherein the solid substrate comprises any non-toxic, non-leaching material.

11. The method of claim 6, wherein the solid substrate comprises a plurality of rigid polymer bead.

12. The method of claim 11, wherein the rigid polymer bead is selected from the group consisting of polyurethane, polymethylmethacrylate, polyethylene or co-polymers of ethylene and other monomers, polyethylene imine, polypropylene, and polyisobutylene.

13. The method of claim 6, wherein the solid substrate comprises one or a plurality of hollow fibers.

14. The method of claim 1, wherein the adsorption media comprises about 90% to about 10 wt. % of activated carbon.

15. The method of claim 1, wherein the cleansed sample has a drug content that is reduced by about 10% to about 100% from the sample.

16. The method of claim 1, wherein the drug intoxication is the result of a drug overdose.

* * * * *